(12) United States Patent
Newell et al.

(10) Patent No.: US 12,005,224 B2
(45) Date of Patent: *Jun. 11, 2024

(54) PINCH CLAMP DEVICES, METHODS, AND SYSTEMS

(71) Applicant: NxStage Medical, Inc., Lawrence, MA (US)

(72) Inventors: Scott W. Newell, Ipswich, MA (US); Dennis M. Treu, Castle Rock, CO (US); Kenneth E. Buckler, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 80 days.

This patent is subject to a terminal disclaimer.

(21) Appl. No.: 17/566,293

(22) Filed: Dec. 30, 2021

(65) Prior Publication Data

US 2022/0193390 A1    Jun. 23, 2022

Related U.S. Application Data

(63) Continuation of application No. 16/185,589, filed on Nov. 9, 2018, now Pat. No. 11,213,669, which is a continuation of application No. 15/517,909, filed as application No. PCT/US2015/055030 on Oct. 9, 2015, now Pat. No. 10,195,418.

(Continued)

(51) Int. Cl.
*A61M 39/28* (2006.01)
*A61M 39/10* (2006.01)
(Continued)

(52) U.S. Cl.
CPC .......... *A61M 39/283* (2013.01); *A61M 39/10* (2013.01); *A61M 39/28* (2013.01);
(Continued)

(58) Field of Classification Search
CPC .... A61M 39/283; A61M 39/10; A61M 39/28; A61M 5/16813; A61M 5/281;
(Continued)

(56) References Cited

U.S. PATENT DOCUMENTS 2,934,305 A   4/1960   Wallace et al.
3,184,214 A   5/1965   King
(Continued)

FOREIGN PATENT DOCUMENTS

DE         3909634 A1    9/1990
DE    102013102084 A1    9/2014
(Continued)

OTHER PUBLICATIONS

International Preliminary Report on Patentability for PCT/US2015/055030 dated Apr. 20, 2017, including the Written Opinion of the International Searching Authority dated Jan. 7, 2016.
(Continued)

*Primary Examiner* — Craig J Price
*Assistant Examiner* — Andrew J Rost
(74) *Attorney, Agent, or Firm* — Potomac Law Group, PLLC

(57) ABSTRACT

A method of controlling flow through a flexible tube includes providing a pinch clamp mechanism including a pinching element and a pinching surface configured to apply a force on the flexible tube when the flexible tube is positioned between the pinching element and the pinching surface. The method also includes displacing the pinching element relative to the pinching surface with a mechanical drive unit and biasing the pinching element toward the pinching surface with a spring.

3 Claims, 12 Drawing Sheets

Related U.S. Application Data

(60) Provisional application No. 62/063,244, filed on Oct. 13, 2014, provisional application No. 62/062,729, filed on Oct. 10, 2014.

(51) Int. Cl.
| | | |
|---|---|---|
| *F16K 7/04* | (2006.01) | |
| *F16K 7/06* | (2006.01) | |
| *F16K 31/528* | (2006.01) | |
| *A61M 39/08* | (2006.01) | |
| *F16K 31/04* | (2006.01) | |

(52) U.S. Cl.
CPC ............. *F16K 7/045* (2013.01); *F16K 7/061* (2013.01); *F16K 7/063* (2013.01); *F16K 31/5288* (2013.01); *A61M 39/08* (2013.01); *F16K 31/04* (2013.01)

(58) Field of Classification Search
CPC ...... A61M 39/284; F16K 7/045; F16K 7/061; F16K 7/065; F16K 7/06; F16K 31/104; F16K 31/528; F16K 7/063
See application file for complete search history.

(56) References Cited

U.S. PATENT DOCUMENTS

| | | | |
|---|---|---|---|
| 4,156,438 A | 5/1979 | Kiesow | |
| 4,176,671 A | 12/1979 | Citrin | |
| 4,209,391 A | 6/1980 | Lipps et al. | |
| 4,259,985 A * | 4/1981 | Bergmann | F16K 7/045 |
| | | | 137/870 |
| 4,300,552 A | 11/1981 | Cannon | |
| 4,372,304 A | 2/1983 | Avakian et al. | |
| 4,429,856 A | 2/1984 | Jackson | |
| 4,430,081 A | 2/1984 | Timmermans | |
| 4,439,179 A | 3/1984 | Lueders et al. | |
| 4,442,954 A * | 4/1984 | Bergandy | F16K 7/045 |
| | | | 222/215 |
| 4,444,198 A | 4/1984 | Petre | |
| 4,479,760 A | 10/1984 | Bilstad et al. | |
| 4,504,038 A | 3/1985 | King | |
| 4,519,792 A | 5/1985 | Dawe | |
| 4,596,374 A | 6/1986 | Thompson et al. | |
| 4,617,115 A | 10/1986 | Vantard | |
| 4,747,950 A | 5/1988 | Guinn | |
| 4,821,996 A | 4/1989 | Bellotti et al. | |
| 4,993,456 A * | 2/1991 | Sule | F16K 7/045 |
| | | | 137/554 |
| 4,997,570 A | 3/1991 | Polaschegg | |
| 5,000,419 A | 3/1991 | Palmer et al. | |
| 5,005,805 A | 4/1991 | Morris et al. | |
| 5,190,071 A | 3/1993 | Sule | |
| 5,326,033 A * | 7/1994 | Anfindsen | F16K 7/065 |
| | | | 239/300 |
| 5,419,237 A | 5/1995 | Jeppsson | |
| 5,725,773 A | 3/1998 | Polaschegg | |
| 5,744,027 A | 4/1998 | Connell et al. | |
| 5,769,385 A | 6/1998 | Burrous et al. | |
| 6,062,218 A * | 5/2000 | Krahbichler | A61M 16/20 |
| | | | 128/205.24 |
| 6,325,775 B1 | 12/2001 | Thom et al. | |
| 6,655,652 B2 | 12/2003 | Meinhof | |
| 6,695,278 B2 | 2/2004 | Ellis | |
| 6,793,194 B1 | 9/2004 | Grinberg | |
| 6,880,804 B1 | 4/2005 | Biggers | |
| 7,371,246 B2 | 5/2008 | Viola | |
| 7,611,505 B2 | 11/2009 | Ranalletta et al. | |
| 7,972,291 B2 | 7/2011 | Ibragimov | |
| 8,287,480 B2 | 10/2012 | Sasaki et al. | |
| 8,387,943 B1 | 3/2013 | Mattheis | |
| 8,398,859 B2 | 3/2013 | López | |
| 8,479,505 B2 * | 7/2013 | McBride | F15B 15/00 |
| | | | 60/659 |
| 8,585,907 B2 | 11/2013 | Raiford et al. | |
| 8,590,558 B2 | 11/2013 | Reinstorff | |
| 8,591,491 B2 | 11/2013 | Moy et al. | |
| 8,636,176 B2 | 1/2014 | Malin et al. | |
| 8,667,887 B2 | 3/2014 | Wiedenmann et al. | |
| 8,789,558 B2 | 7/2014 | Volker | |
| 8,821,719 B2 | 9/2014 | Becker | |
| 8,834,718 B2 | 9/2014 | Randall et al. | |
| 8,877,061 B2 | 11/2014 | Lovell | |
| 8,961,444 B2 | 2/2015 | Chapman et al. | |
| 8,998,836 B2 | 4/2015 | Chapman et al. | |
| 9,028,439 B2 | 5/2015 | Wich-Heiter | |
| 9,044,544 B2 | 6/2015 | Lo et al. | |
| 9,044,586 B2 | 6/2015 | Egley et al. | |
| 9,067,051 B2 | 6/2015 | Loth et al. | |
| 9,415,151 B2 | 8/2016 | Schlaeper et al. | |
| 9,435,459 B2 | 9/2016 | Bedingfield | |
| 9,474,846 B2 | 10/2016 | Steger | |
| 9,724,458 B2 | 8/2017 | Grant et al. | |
| 9,782,577 B2 | 10/2017 | Bedingfield | |
| 9,789,300 B2 | 10/2017 | Lauer | |
| 9,808,566 B2 | 11/2017 | Gronau et al. | |
| 9,814,818 B2 | 11/2017 | Weis et al. | |
| 9,822,709 B2 | 11/2017 | Broman | |
| 9,889,287 B2 | 2/2018 | Guala | |
| 9,907,894 B2 | 3/2018 | Mishima | |
| 9,913,939 B2 | 3/2018 | Bachmann et al. | |
| 10,161,532 B2 | 12/2018 | Patthey | |
| 10,195,418 B2 * | 2/2019 | Newell | F16K 7/045 |
| 10,863,941 B2 | 12/2020 | Jensen et al. | |
| 2004/0163711 A1 | 8/2004 | Varone et al. | |
| 2006/0197040 A1 | 9/2006 | Brieske | |
| 2011/0198350 A1 | 8/2011 | Meisberger et al. | |
| 2011/0245916 A1 | 10/2011 | Min et al. | |
| 2012/0018654 A1 | 1/2012 | Wennberg et al. | |
| 2012/0278006 A1 | 11/2012 | Weatherbee et al. | |
| 2013/0009079 A1 | 1/2013 | Ams et al. | |
| 2013/0037142 A1 | 2/2013 | Farrell | |
| 2013/0334138 A1 | 12/2013 | Cicchello et al. | |
| 2014/0299798 A1 | 10/2014 | Opfer et al. | |
| 2015/0107263 A1 | 4/2015 | Broman | |
| 2015/0190623 A1 | 7/2015 | Jeda et al. | |
| 2015/0196750 A1 | 7/2015 | Jeda et al. | |
| 2015/0232798 A1 | 8/2015 | Zhou et al. | |
| 2016/0010755 A1 | 1/2016 | Maenz et al. | |
| 2016/0095970 A1 | 4/2016 | Kelly et al. | |
| 2016/0201781 A1 | 7/2016 | Cao et al. | |
| 2016/0206868 A1 | 7/2016 | Guala | |
| 2016/0243347 A1 | 8/2016 | Geiger et al. | |
| 2016/0310656 A1 | 10/2016 | Vinci | |
| 2016/0319954 A1 | 11/2016 | Smith | |
| 2016/0354597 A1 | 12/2016 | Schlaeper et al. | |
| 2016/0362234 A1 | 12/2016 | Peret et al. | |
| 2017/0080139 A1 | 3/2017 | Gößmann et al. | |
| 2017/0095602 A1 | 4/2017 | Ishizaki et al. | |
| 2017/0136169 A1 | 5/2017 | Lauer | |
| 2017/0340796 A1 | 11/2017 | Etzdorf | |
| 2017/0368249 A1 | 12/2017 | Bourne | |
| 2018/0093029 A1 | 4/2018 | Abel et al. | |
| 2018/0140766 A1 | 5/2018 | Mochizuki et al. | |

FOREIGN PATENT DOCUMENTS

| | | |
|---|---|---|
| EP | 3243536 A1 | 11/2017 |
| EP | 3302614 A2 | 4/2018 |
| EP | 3319657 A1 | 5/2018 |
| JP | 2016010599 A | 1/2016 |
| JP | 6070348 B2 | 2/2017 |

OTHER PUBLICATIONS

International Search Report and Written Opinion for International Application No. PCT/US2015/055030 dated Jan. 7, 2016.

* cited by examiner

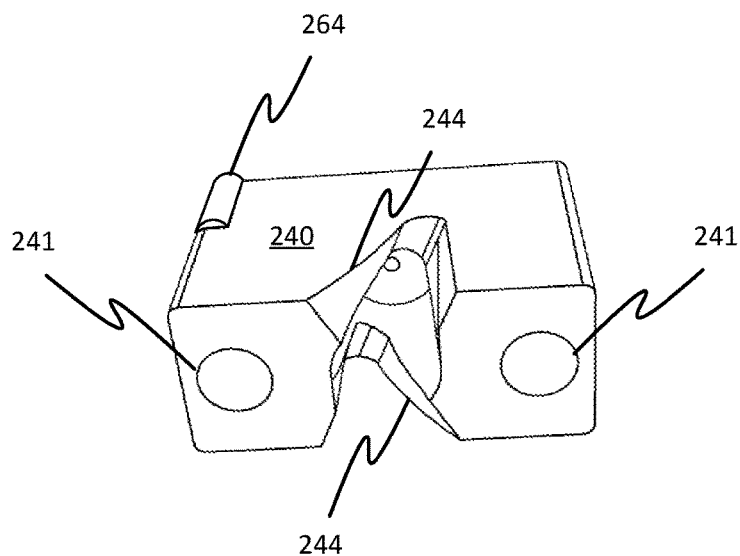
Fig. 12
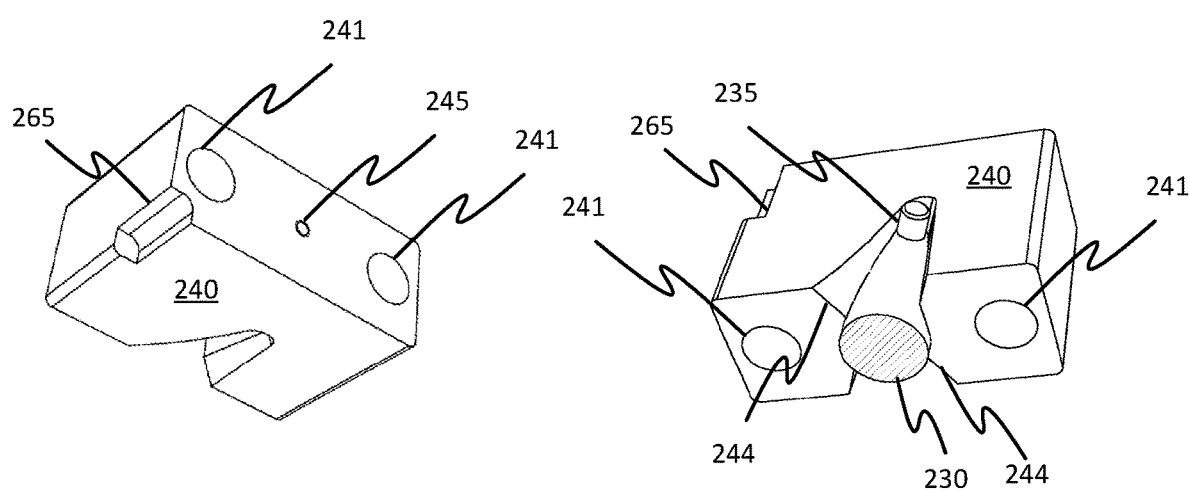
Fig. 13
Fig. 14

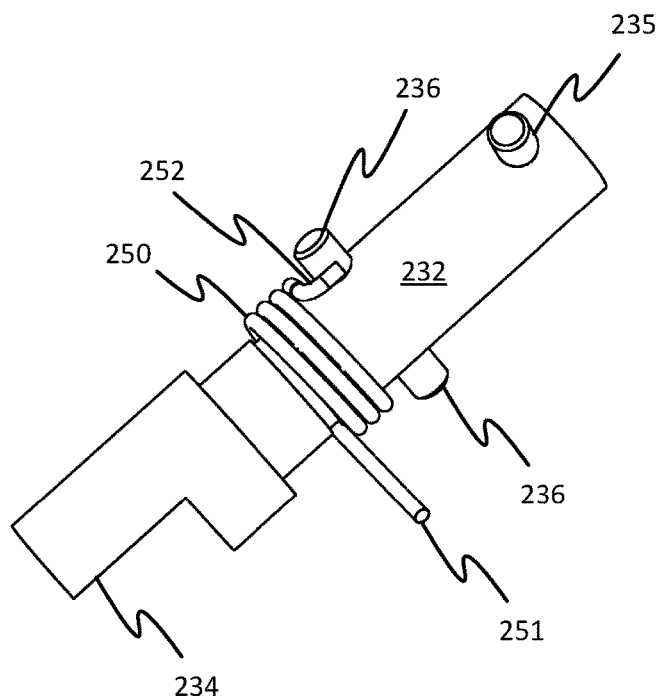
Fig. 15
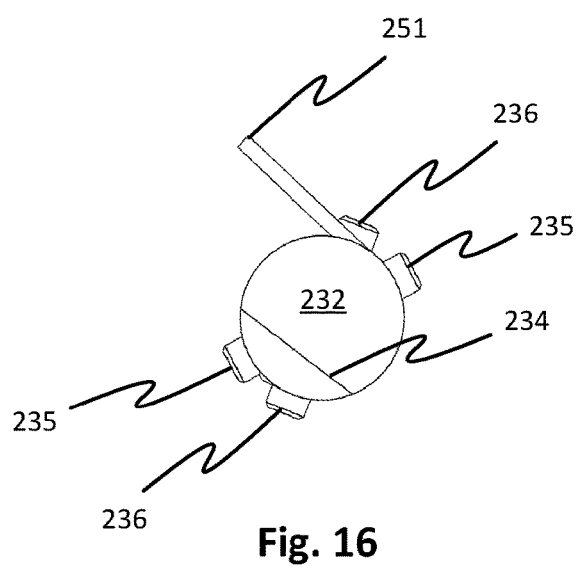 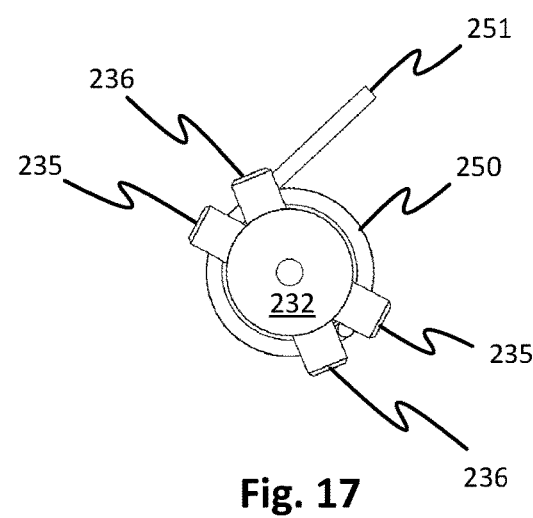
Fig. 16  Fig. 17

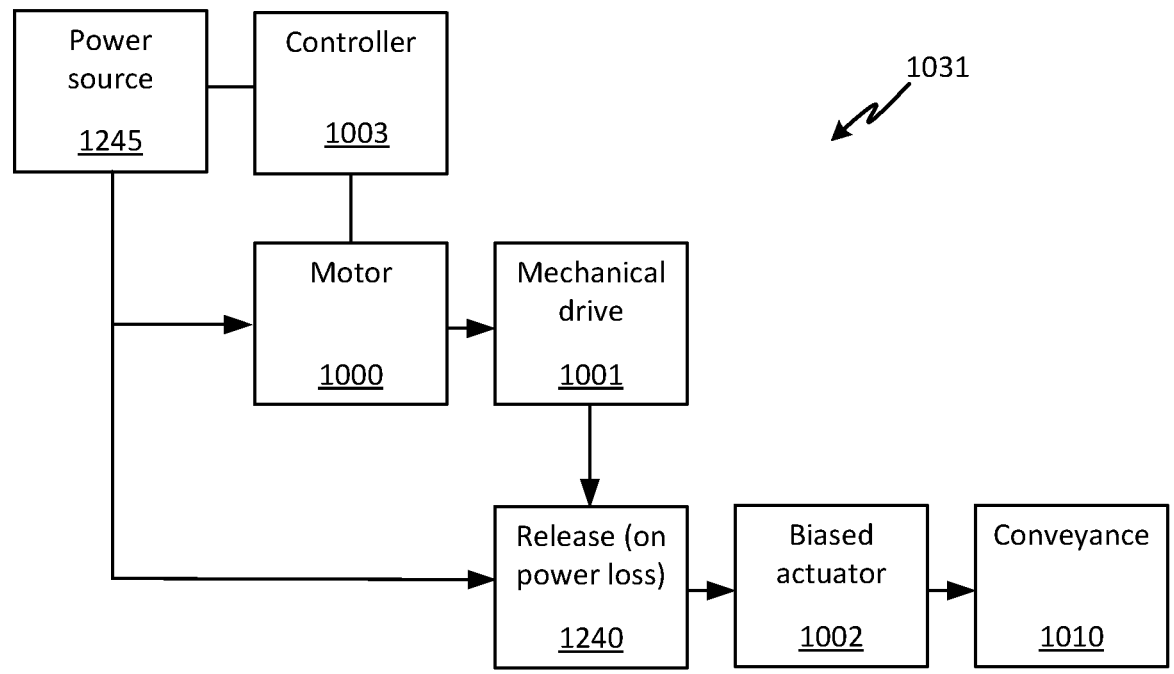
Fig. 24
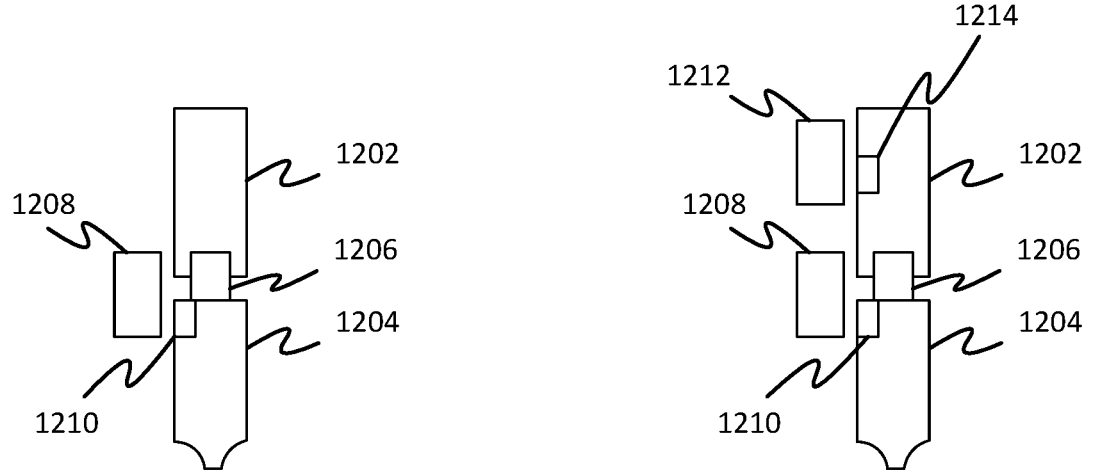
Fig. 26A                    Fig. 26B

PINCH CLAMP DEVICES, METHODS, AND SYSTEMS

RELATED APPLICATIONS

This application is a continuation of application Ser. No. 16/185,589, filed on Nov. 9, 2019, which is a continuation of U.S. application Ser. No. 15/517,909, filed on Apr. 7, 2017, now U.S. Pat. No. 10,195,418, issued Feb. 5, 2019, which is a U.S. national stage filing under 35 U.S.C. § 371 of International Application No. PCT/US2015/055030 filed Oct. 9, 2015, which claims the benefit of U.S. Provisional Application Nos. 62/063,244 filed Oct. 13, 2014 and 62/062,729 filed Oct. 10, 2014, all of which are hereby incorporated by reference in their entireties.

BACKGROUND

Pinch clamps or valves that use a pinching motion to control the flow of a fluid through a compressible tube are known. Actuated pinch valves use an actuator to displace a pinching element against a portion of the outer wall of the compressible tube. The pinching element progressively collapses the outer wall portion against an opposing section of the pinch valve or other support structure to regulate fluid flow through the tube. Due to the separation of the pinching element from the fluid flowing through the compressible tube, cross-contamination is prevented, which renders actuated pinch valves preferable for use in various medical devices, including, for example, dialysis equipment, intravenous systems, blood analyzers, etc.

Pinch valve actuators typically employ an electrical solenoid that is counterbalanced by a spring. The spring applies the force for pinching and solenoid holds the actuator against the spring to open the valve. Thus, when power is applied to the solenoid, the valve is open and the valve is closed by selective deactivation of the solenoid or by loss of power. This functionality serves as a safeguard by halting the flow of fluids when system power is lost. This can be critical in medical treatment systems.

SUMMARY

The following summary pertains to representative embodiments and is not an exhaustive list thereof. Embodiments of the present disclosure provide a linearly actuated pinch clamp comprising a housing, a motor connected to the housing, a mechanical drive unit connected to the motor for converting a rotary motion of the motor to a linear motion and for introducing a mechanical advantage to the motion of the motor, and a pinching element having a body and a pinching surface. The pinching element body is coupled to the mechanical drive unit and slidably mounted to the housing such that the pinching element is linearly displaceable by the mechanical drive unit between a first position and a second position where the pinching surface cooperates with a fixed surface to pinch closed a flexible tube.

Further embodiments of the present disclosure also provide a linearly actuated pinch clamp comprising a housing having a flange, a motor connected to the housing, a mechanical drive unit connected to the motor for converting a rotary motion of the motor to a different rate and/or type of motion which may include an increase in mechanical advantage to the motion of the motor. A coupling element may including a cam surface and be connected to the mechanical drive unit and slidably and mounted to the housing. A rotationally displaceable pinching element may engage with the cam surface and be rotated thereby to effect pinching.

Embodiments of the present disclosure also provide a pinch clamp system that includes a power supply, a microcontroller coupled to the power supply; an energy storage device coupled to the power supply; a motor driver coupled to the energy storage device; and a linearly actuated pinch clamp coupled to the motor driver and the microcontroller. The pinch clamp includes a motor, a mechanical drive unit connected to the motor for converting a rotary motion of the motor to a linear motion and for introducing a mechanical advantage to the motion of the motor; a displaceable pinching element coupled to the mechanical drive unit and including a pinching surface, the pinching element being displaceable between a first position and a second position where the pinching surface cooperates with a fixed surface to pinch closed a flexible tube; and a sensor to measure a position of the pinching element. The system further includes a switch, coupled to the power supply, the microcontroller and the motor driver, to pass commands from the microcontroller to the motor driver when the power supply voltage remains above a predetermined threshold, and to provide a command to the motor controller to move the pinching element to the second position when the power supply voltage falls below the predetermined threshold.

There has thus been outlined, rather broadly, certain embodiments of the disclosure in order that the detailed description thereof herein may be better understood, and in order that the present contribution to the art may be better appreciated.

Before explaining at least one embodiment of the disclosure in detail below, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

BRIEF DESCRIPTION OF THE DRAWINGS

FIGS. 12, 13 and 14 are perspective, top and bottom views of a coupling block, in accordance with the embodiment depicted in FIGS. 10 and 11.

FIGS. 15, 16 and 17 are perspective, top and bottom views of a pinching element, in accordance with the embodiment depicted in FIGS. 10 and 11.

FIG. 24 is a block diagram of a valve according to the present disclosure in which an intermediate connection between the mechanical drive and a biased actuator causes the actuator to close the conveyance, thereby avoiding the need for energy storage.

FIGS. 26A and 26B show an alternative arrangement of an electromagnet for a variant of the embodiment of FIGS. 25A and 25B.

DETAILED DESCRIPTION

Figure 2:
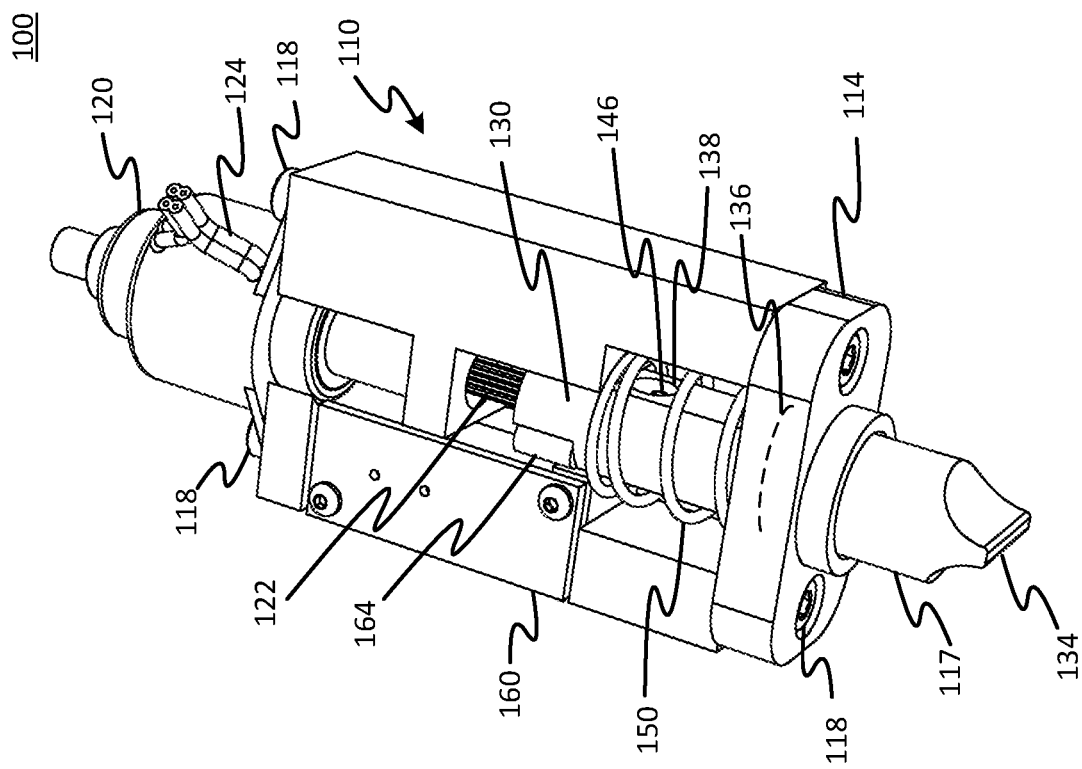
FIGS. 1 and 2 are perspective views of a linearly actuated pinch clamp in open and closed positions, respectively, in accordance with an embodiment of the present disclosure.
Figure 1:
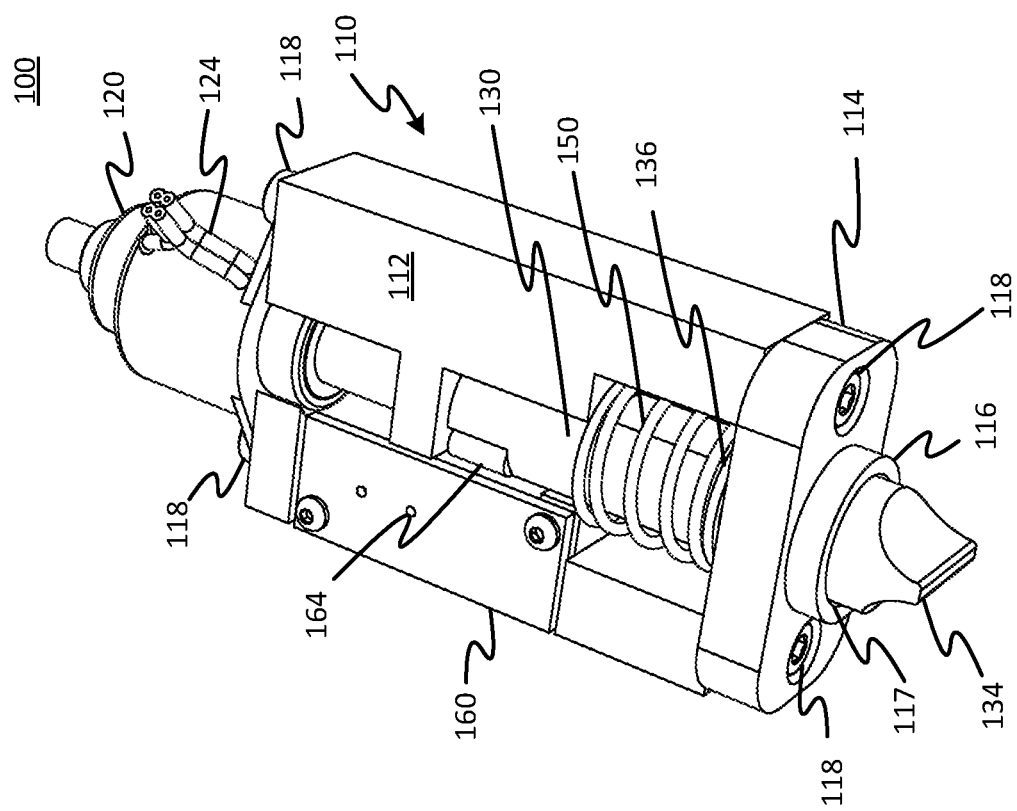

The disclosure will now be described with reference to the drawing figures, in which like reference numerals refer to like parts throughout.

Embodiments of the present disclosure advantageously provide a linearly actuated pinch clamp that is small, lightweight, reliable, low cost and simple to control, provides clamp pinching element position information, and consumes less power and produces less noise than solenoid-based devices. Embodiments of the present disclosure also ensure that the linearly actuated pinch clamp is automatically closed upon detection of a power failure.

Figure 21:
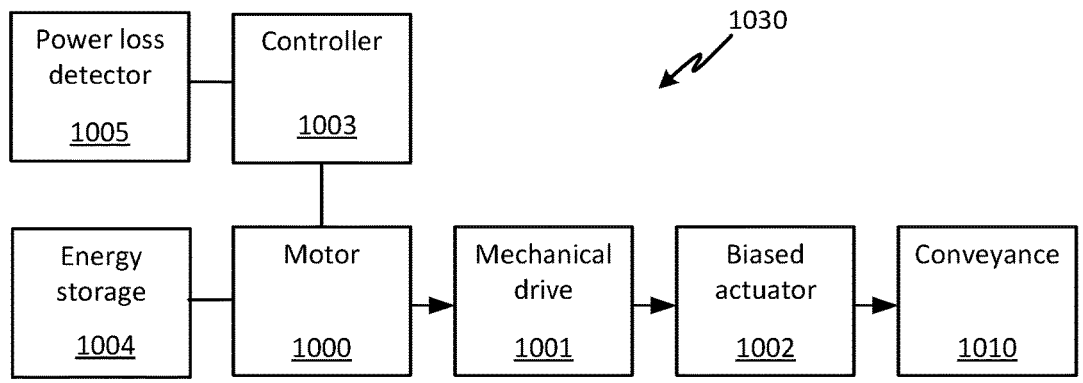
FIG. 21 is block diagram of a valve according to the present disclosure.

FIG. 21 is a block diagram providing an overview of the disclosed pinch clamp. The clamp 1030 comprises a motor 1000, which can be a conventional motor, a stepper motor, etc. The output of motor 1000 is connected to drive a mechanical drive unit 1001 that either converts the motion of the motor 1000 to a different kind of motion (e.g., linear-to-rotary or linear-to-curvilinear) with or without force multiplication. The force multiplication may include the generation of mechanical advantage provided by the mechanism of the mechanical drive 1001. Examples of such force-multiplying mechanisms include gear trains, worm drives, cranks, linkages, chain drives, screw drives, etc. The mechanical drive converted mechanical output of the mechanical drive 1001 is applied to an actuator, for example, a pinching element that pinches a flexible tube (which is an example of a conveyance 1010) to block the flow of fluid therethrough, or a valve portion. In particular embodiments, the mechanical drive unit 1001 includes a screw drive, such as used in many linear actuators. In other embodiments, the mechanical drive unit 1001 comprises a set of gears, such as a rack and pinion arrangement. In still further embodiments, the mechanical drive includes a cam and follower arrangement. These embodiments are merely illustrative and may of a variety of different types within the scope of the disclosed and claimed subject matter.

The output of mechanical drive unit 1001 is applied to a biased actuator 1002 which applies a biasing force of a spring, elastomer, or other equivalent biasing device, to a member that alters the state of the conveyance 1010 to stop a flow therethrough. The arrangement between the biased actuator 1002 and the mechanical drive 1001 is such that the mechanical drive 1001 is able to apply a force against the biasing device to retract and open the fluid conveyance 1010. The fluid conveyance can be a flexible bag, a tube, or other device for conveying fluid. Preferably the motor 1000 and mechanical drive 1001 are configured such that the spring or other biasing device of the biased actuator 1002 is not able to force itself into a relaxed state when the motor 1000 is at rest. In this way, the motor 1000 can be operated when the state of the conveyance 1010 is to be altered. In embodiments, the biased actuator 1002 includes a pinching element that is forced against a flexible tube type of conveyance 1010 wherein the tube is pinched in cooperation with a fixed member. In embodiments, the pinching element may be two opposing pinching elements the open and close in a gripper or scissor fashion to pinch claim tube. In other embodiments, the pinching element may be a single element that cooperates with a fixed stationary element between which the tube is compressed.

In embodiments the pinching element is linearly displaceable. In other embodiments the pinching element is rotationally displaceable. Various kinematic mechanisms can produce combinations or types of motion and may be employed with the pinching element. In any of these embodiments, the pinching element may be a single element that cooperates with a fixed element or may be one of multiple elements that cooperatively pinch the tube. In any of the embodiments biased actuator 1002 may include an urging element such as a spring, elastomer, or arrangement of magnets, effective to produce a biasing force that biases the actuator (e.g., pinching element or elements) to a closed position; i.e., a position that closes the conveyance 1010. The motor 1000 applies a force to overcome the bias of the urging thereby permitting the tube (generally, the conveyance 1010) to open. The biasing element may be selected to provide precisely the force, applied to an actuator of the biased actuator 1002 (e.g., pinching element or elements) to ensure a reliable seal of the conveyance 1010 (e.g., flexible tube). Advantageously, the mechanical drive 1001 may be selected such that no power is required to maintain the pinching element or elements in the open or closed position. In other words, the motor is deactivated after an open or closed position is reached. In embodiments, this is assured by a suitable selection of the mechanical drive 1001 such that internal friction of the mechanical drive 1001, the motor 1000, and or the biased actuator 1002, or interfering resistance of any or all of these, prevents movement of the biased actuator unless the motor 1000 is used to drive it.

Motor 1000 is controlled via signals and/or power from a controller 1003, which is connected to an energy storage device 1004 and a power loss detector 1005. The controller 1003 may include a motor drive that applies both power and command signals to the motor 1000, such as in a stepper motor configuration. Alternatively, the controller 1003 may apply electrical power to the motor in a feedback or feedforward control configuration. The motor 1000 and mechanical drive unit 1001 may maintain the biased actuator 1002 in the open and/or the closed position without the application of power. A "fail safe" feature closes the clamp if power is lost. If a power failure occurs, controller 1003 receives a signal from power loss detector 1005. In response, controller 1003 applies energy stored in the energy storage device 1004 to operate the motor 1000 to move biased actuator 1002 to the closed position. For example, the energy storage 1004 may be a mechanical energy store such as a spring, pneumatic pressure vessel, a battery, or a capacitor.

In any of the embodiments, a biased actuator (or equivalent thereof) may be configured such that the release of the bias device, or equivalent, is such that the force applied to the conveyance is determined by the selected bias force of the bias device, or equivalent. In any of the embodiments, the motor and mechanical drive, or equivalents thereof may displace the biased actuator, or equivalent thereof, in a progressive manner.

Figure 22A:
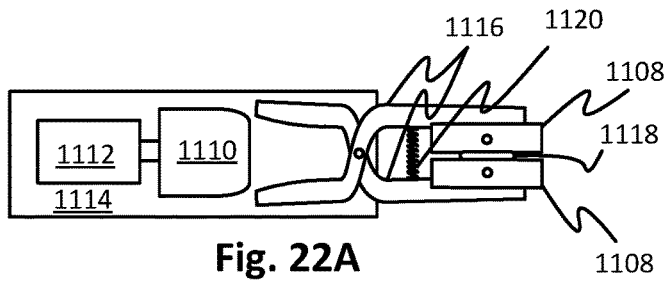
FIGS. 22A and 22B show another type of pinch clamp embodiment which may be used in some of the embodiments of the present disclosure.
Figure 22B:
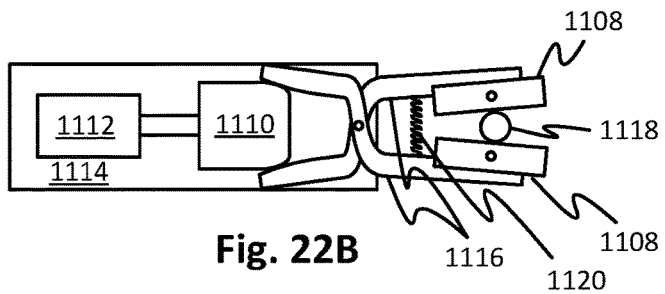

FIGS. 22A and 22B show a pinching device with a chassis 1114 and a linear drive 1112 affixed thereto. When the drive 1112 moves the cam member 1110 to the position shown in FIG. 22A, this permits a force of a spring 1120 to move pivot arms 1116 to move pinching members 1108 together thereby to pinch a tube 1118. The linear drive 1112 moves progressively from the position shown in FIG. 22A to the position shown in FIG. 22B and back again under control of a controller. In FIG. 22B, the linear drive 1112 has moved the cam member 1110 to urge the pivot arms 1116 against the force of a spring 1120 thereby to displace pinching members 1108 in opposite directions away from the tube. The cam member thereby takes up the force generated by the spring 1120 so that the tube 1118 is released and fluid is able to flow. In each of the positions of 22A and 22B, the motor may remain at rest, with the linear drive 1112, the cam member 1110, and the pivot arms 1116 providing sufficient resistance (friction) to prevent the spring 1120 from moving the pivot arms 1116 without the action of the linear drive 1112. Thus, the controller (not shown but which may be any suitable type of controller) may produce a drive current to the linear drive (which may include, for example, an electric motor) to cause the motor to run, then stop, then run in reverse, then stop in order to selectively achieve the states shown in FIGS. 22A and 22B.

Figures 23A, 23B:
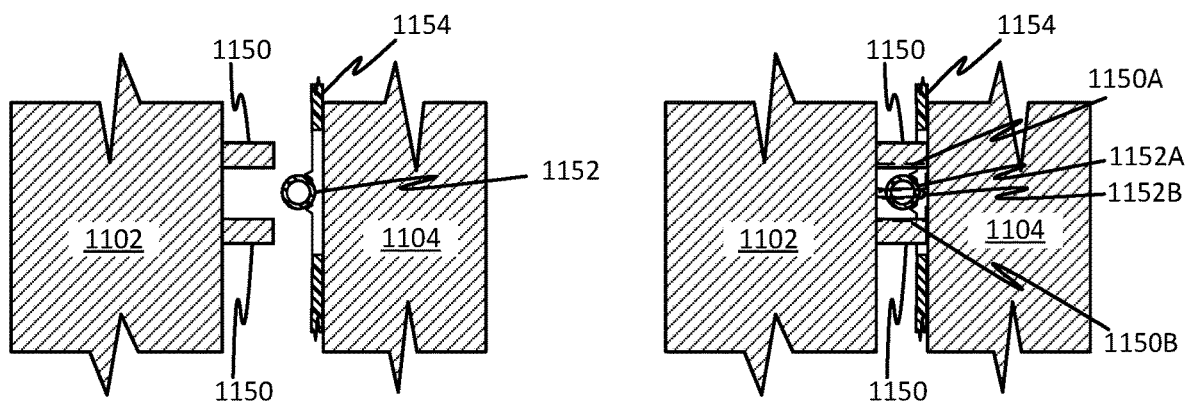
FIGS. 23A and 23B shows an advantageous system that employs a pinch clamp according to embodiments of the present disclosure.

FIGS. 23A and 23B show a device, for example, a medical device with first and second parts 1102 and 1104 that movable together and apart such that a pair of pinching members 1150 surrounds a tube 1152 (as in FIG. 23B) or moves away from the tube 1152 FIG. 23A. The tube 1152 may be carried on a support 1154 such as a cartridge or cassette carrying various fluid circuit elements. The support may, in turn, be supported by second part 1104. Alternatively the tube 1152 may be supported directly by the second part 1104. When one or both of the parts 1102 and 1104 are brought together, for example by manually forcing them or by means of a motor (not shown). The positions of the parts 1102 and 1104 may adapted to facilitate loading of the support 1154 (or tube 1152, alone) and the positions of the parts 1102 and 1104 may be adapted for operation of a system in which fluid flows through the tube 1152. The pinching members 1150, in the configuration shown in FIG. 23A may open and close about the tube according to any of the embodiments described herein. The pinching members are shown in open position at 1152A and in a closed position as dashed lines at 1152B. The arrangement of FIGS. 23A and 23B is such that no force needs to be resisted between the parts 1102 and 1104 in order to close the tube 1152. Note that part 1102 may carry multiple pinch clamps and part 1104 may carry multiple tubes 1152 all of which may be operable selectively and independently. Note that the pinching members 1150 are merely figurative and can be the pinching elements of the pinch clamp embodiment 200 described below with reference to FIGS. 10-18 or other embodiments.

FIGS. 1-9 depict various views of a linearly actuated pinch clamp 100, in accordance with an embodiment of the present disclosure. The pinch clamp 100 regulates the flow of liquid through a flexible (i.e., compressible) tube 50, and, in this embodiment, the pinch clamp 100 cooperates with a fixed surface 75, such as, for example, a portion of a hemodialysis machine through which flexible tube 50 is routed, to control the fluid flow. The pinch clamp 100 is selectively adjustable to provide an open position and a closed position, and, in certain embodiments, a plurality of intermediate positions.

The pinch clamp 100 includes a housing 110 that has a body 112 and a lower plate 114 including a circular flange 116 with a central bore 117. The housing body 112 is shown partially transparent in FIGS. 3 and 4 to facilitate illustration of the internal components of the pinch clamp 100. The lower plate 114 is attached to the housing body 112 via screws 118 or other known attachment means. A motor/mechanical drive unit 120, such as a stepper motor linear actuator as shown at 120, is attached to housing body 112 via screws 118 or other known attachment means, and has an output shaft 122 and power leads 124. In certain embodiments, a stepper motor linear actuator includes a bipolar motor, and the power leads 124 include four wires, two for each phase. In other embodiments, the stepper motor linear actuator used as motor/mechanical drive unit 120 includes a unipolar motor, and the power leads 124 include six wires, three for each phase.

In one embodiment, the motor/mechanical drive 120 is a Series 19541-05-905 captive, bipolar stepper motor linear actuator available from Haydon Kerk Motion Solutions of Waterbury, CT, USA, having a 0.544 inch stroke, a 15° step angle and an operating voltage of 5 VDC. Other stepper motor linear actuators may also be used, such as, for example, non-captive, external, unipolar, 12 VDC operating voltage, etc. Generally, motor/drive units such as stepper motor linear actuators include a stator, a rotor having a nut attached to it, and a threaded lead screw coupled to the nut and an output shaft. The rotor includes a permanent magnet, and the stator coils are sequentially energized, via the power leads, to incrementally turn the rotor in one direction or the other. As the rotor turns, the nut and threaded lead screw convert the rotational motion of the rotor into linear motion of the output shaft.

A linearly displaceable pinching element 130 is at least partially enclosed within the housing body 112, and has a body 132, a pinching surface 134 at a distal end, and a shoulder 136 disposed above the pinching surface 134. A spring 150, such as, for example, a helical compression spring, at least partially surrounds the pinching element body 132, and has a proximal end 151 that abuts a portion of the housing body 112, and a distal end 152 that abuts the pinching element shoulder 136. As shown more clearly in FIGS. 6, 8 and 9, the pinching element body 132 defines a longitudinal bore 131 and a transverse bore 138. The longitudinal bore 131 partially extends into the pinching element body 132 from a proximal end, and the transverse bore 138 intersects the longitudinal bore 131 and extends completely through the pinching element body 132.

A coupling block 140 is slidingly arranged within the longitudinal bore 131, and includes a body 142 defining a transverse bore 144 in which a pin 146 is disposed. The proximal end of the coupling block 140 is connected to the output shaft 122 of the motor/drive unit 120, using, for example, a threaded connection. The length of the coupling block pin 146 is greater than the width of the coupling block body 142, and the diameter of the coupling block pin 146 is smaller than the diameter of the transverse bore 138 of the pinching element body 132. The coupling block pin 146 thus allows a limited range of coupling block 140 motion within the longitudinal bore 131. As shown more clearly in FIGS. 8 and 9, which are perspective longitudinal sectional views of several components of the linearly actuated pinch clamp depicted in FIG. 5, in open and closed positions, respectively, the upper surface 139 of the transverse bore 138 interferingly engages the coupling block pin 146 when the coupling block is moved by the motor/mechanical drive 120 is moved in the proximal direction to pull the pinching surface 134 away from the tube 50. The coupling block pin 146 is positioned between the lower surface 137 of the longitudinal bore 131 and the upper surface of the longitudinal bore 131 when the coupling block 140 is driven in the distal direction to release the pinching element 130 thereby to permit the spring 150 to urge the pinching surface 124 against the tube 150. The longitudinal dimension of the transverse bore 138 is substantially greater than the diameter of the coupling block pin 146 to provide play sufficient to allow the pinching element to transmit the force of the spring 150 to the task of pinching the tube 50 without interference by the coupling block pin.

The pinch clamp 100 also includes a circuit board 160, attached to the housing body 112, on which a magnetoresistive sensor 162 is mounted. In one embodiment, the magnetoresistive sensor 162 is a digital position sensor, such as, for example, a Model KMA36 universal magnetic encoder available from Measurement Specialties of Hampton, VA, USA, that determines the position of the pinching element 130 by sensing the position of an external magnet 164 mounted within a recess 133 in the pinching element body 132. In one embodiment, the external magnet 164 is a cylinder magnet, while in another embodiment, the external magnet 164 is a magnetic pole strip. A pole pitch of 5 mm or less may be used; other pole pitches are also contemplated. Power and data connections to and from the magnetoresistive sensor 162 are provided by an electrical connector 166 mounted on circuit board 160.

Figure 20:
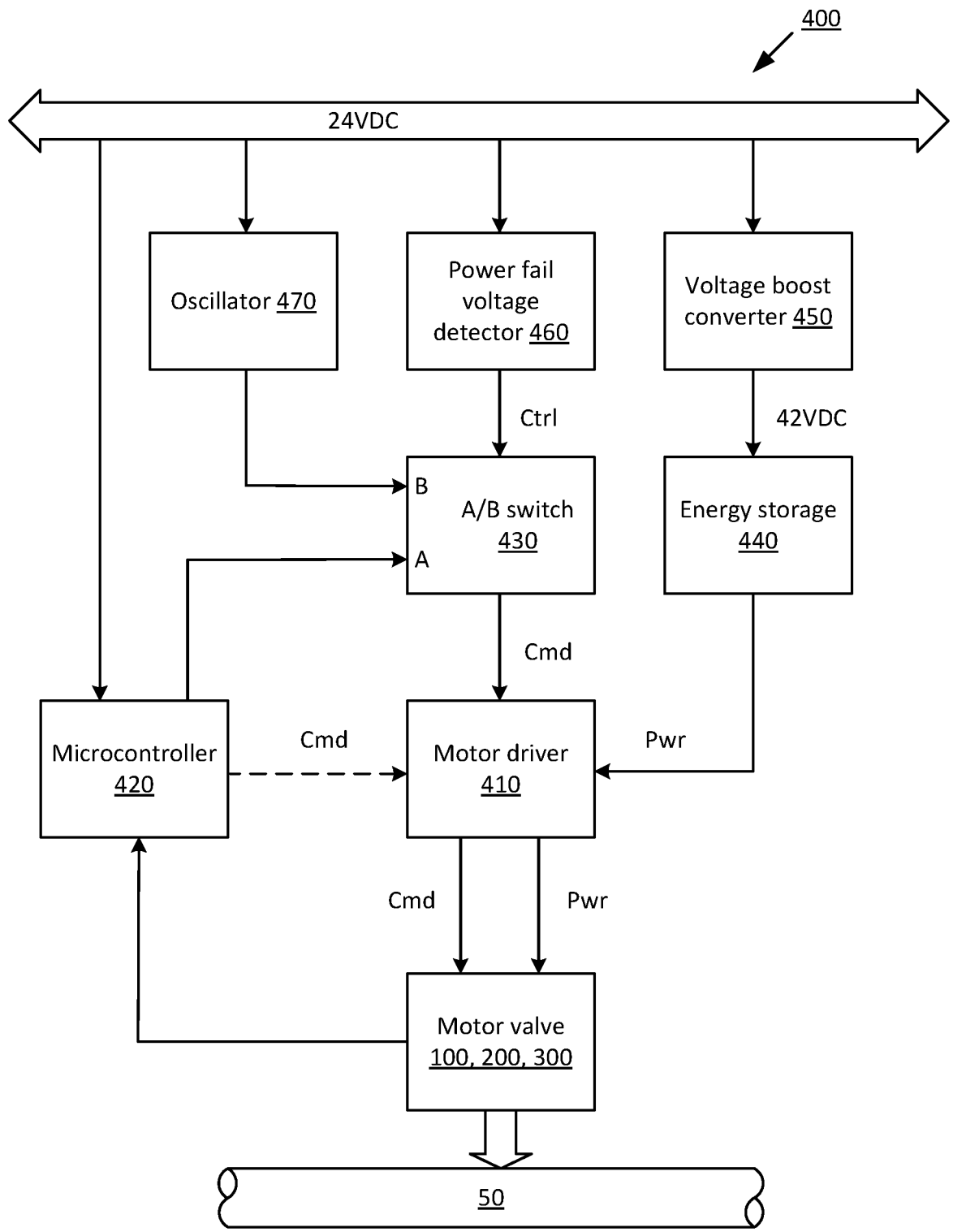
FIG. 20 presents a block diagram of a linearly actuated pinch clamp system, in accordance with an embodiment of the present disclosure.

A microcontroller (not shown for clarity in FIGS. 1-4) is coupled to the pinch clamp 100, via the connector 166, and receives pinching element position measurement data from the magnetoresistive sensor 162. The microcontroller determines the position of the pinching element 130, and provides position commands to a motor driver (not shown for clarity in FIGS. 1-4) coupled to the stepper motor linear actuator 120 via power leads 124. The functionality provided by the microcontroller may be incorporated into a microprocessor onboard the device in which the pinch clamp 100 is employed. The motor driver converts the position commands from the microcontroller into drive signals for the stepper motor linear actuator 120, and then provides those drive signals via power leads 124. The motor driver may include a power supply, logic and switching circuitry, a clock pulse source, etc., and may be a bipolar drive, a unipolar drive, a constant voltage or an L/R drive, a chopper drive, a microstepping drive, etc. The motor driver may be coupled directly or indirectly to a DC supply voltage source. The operation of the microcontroller and motor driver may be as explained in more detail below with respect to FIG. 20.

Figure 3:
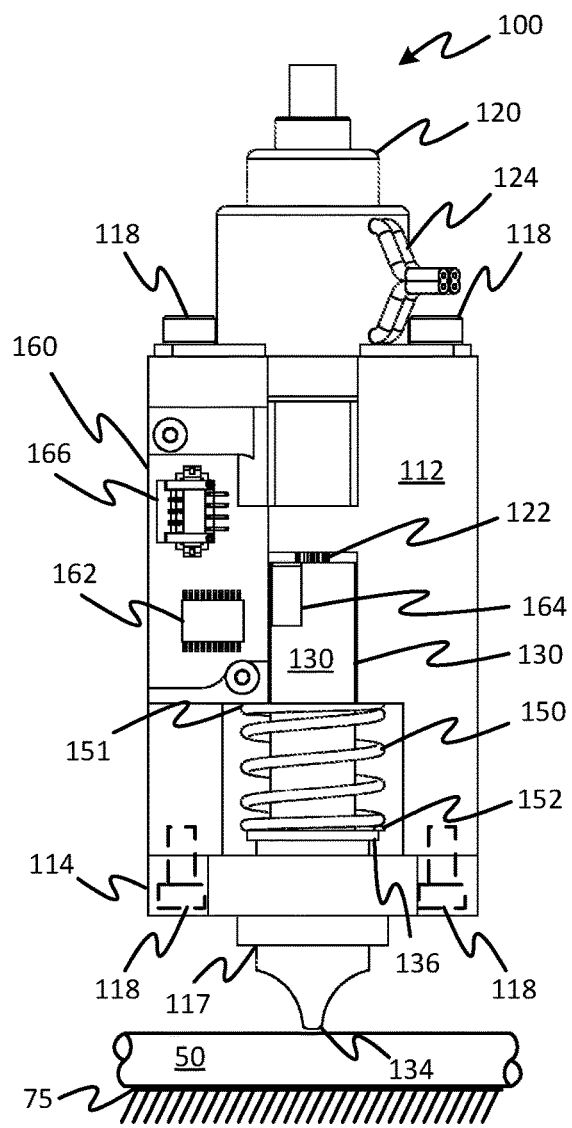
FIGS. 3 and 4 are partial cross-sectional views of a linearly actuated pinch clamp in open and closed positions, respectively, in accordance with the embodiment depicted in FIG. 1.
Figure 4:
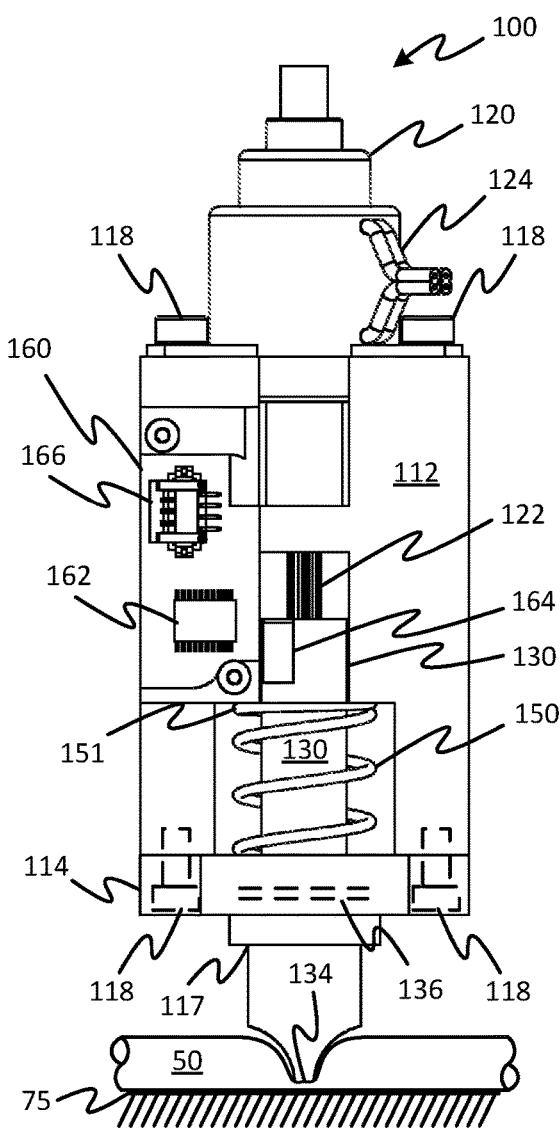
Figure 5:
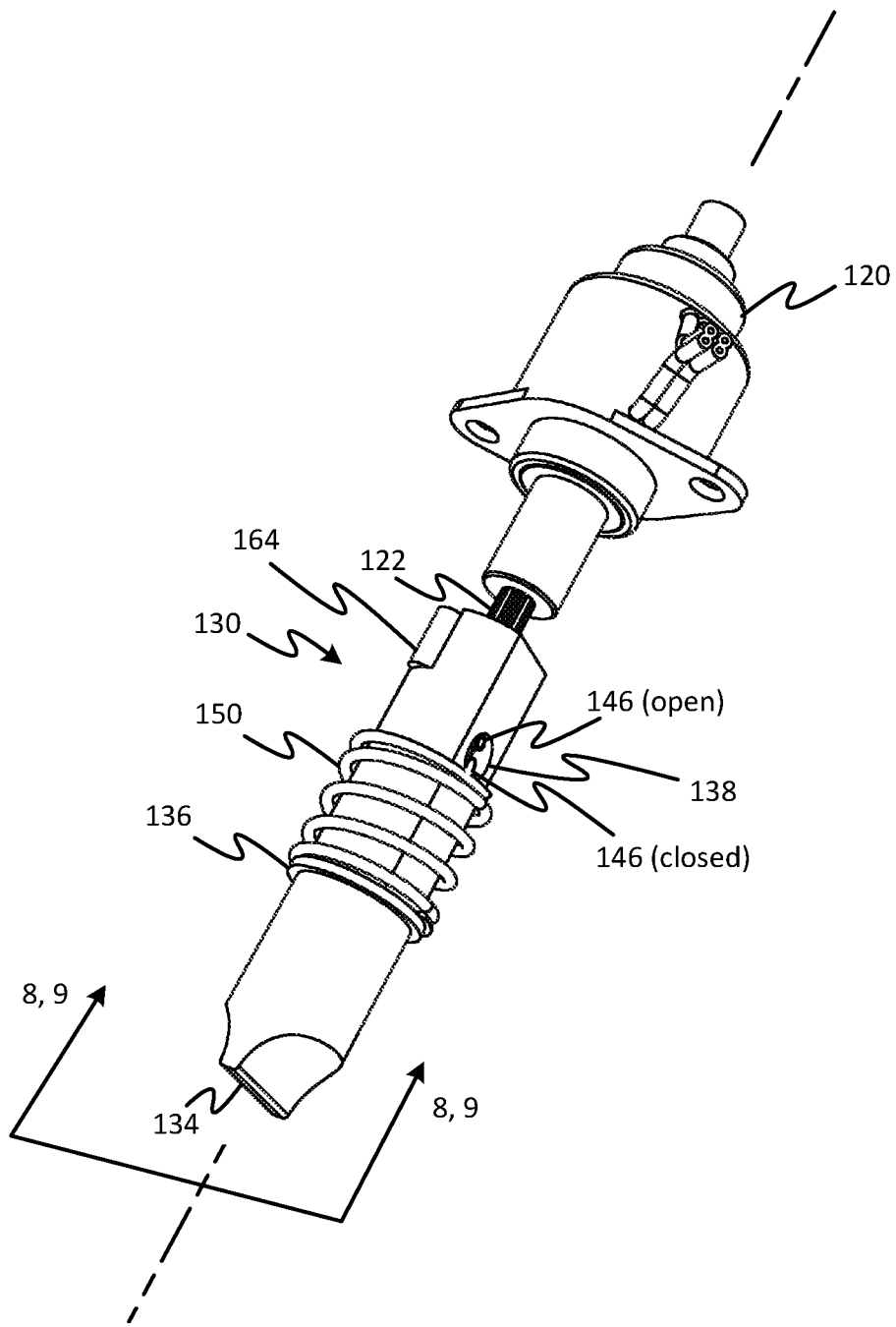
FIG. 5 is a perspective view of several components of a linearly actuated pinch clamp, in accordance with the embodiment depicted in FIGS. 1 and 2.
Figure 6:
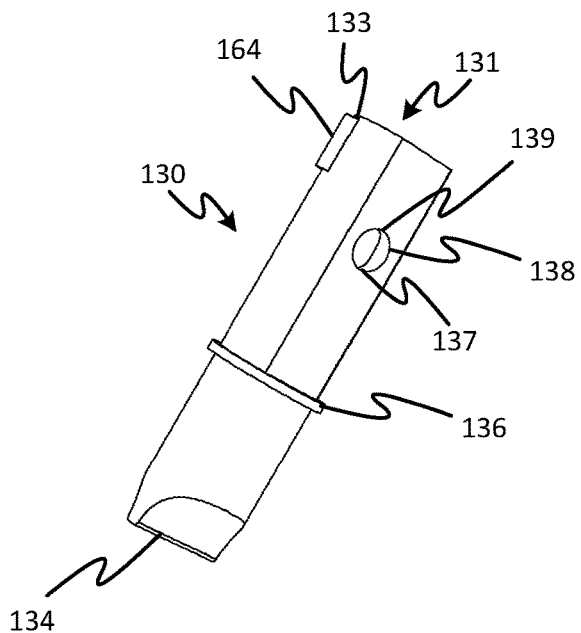
FIG. 6 is a perspective view of a pinching element, in accordance with the embodiment depicted in FIGS. 1 and 2.
Figure 7:
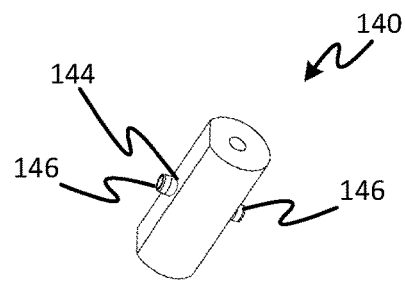
FIG. 7 is a perspective view of a coupling block, in accordance with the embodiment depicted in FIGS. 1 and 2.
Figure 8:
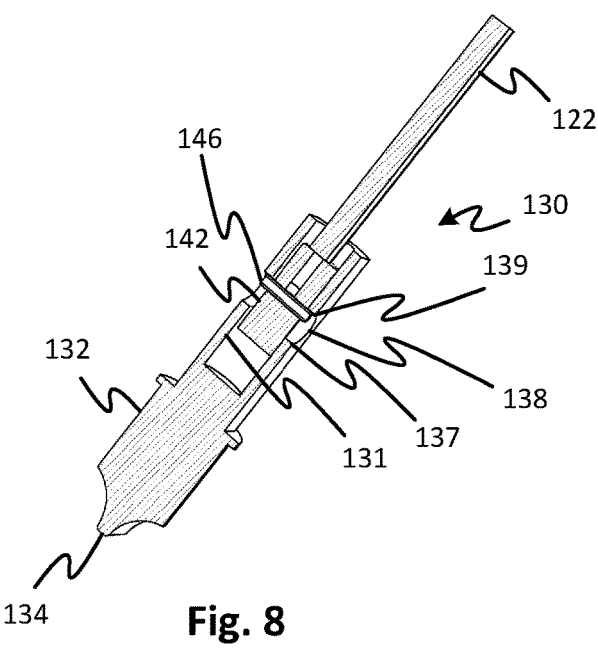
FIGS. 8 and 9 are perspective longitudinal sectional views of several components of the linearly actuated pinch clamp depicted in FIG. 5, in open and closed positions, respectively, in accordance with the embodiment depicted in FIGS. 1 and 2.
Figure 9:
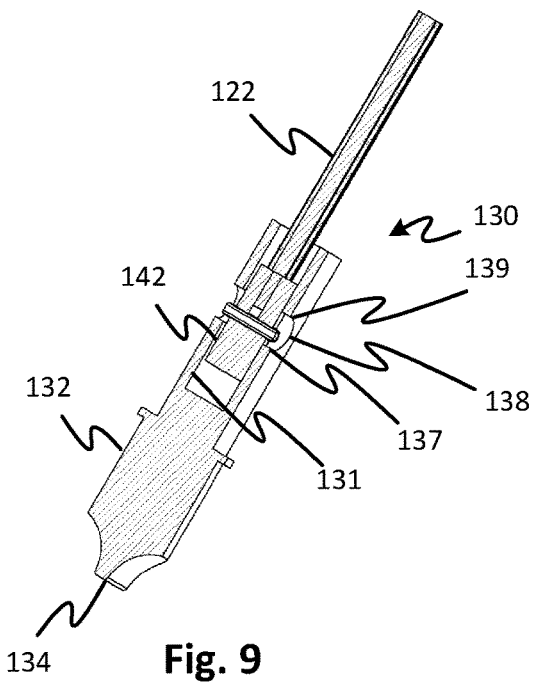
Figure 11:
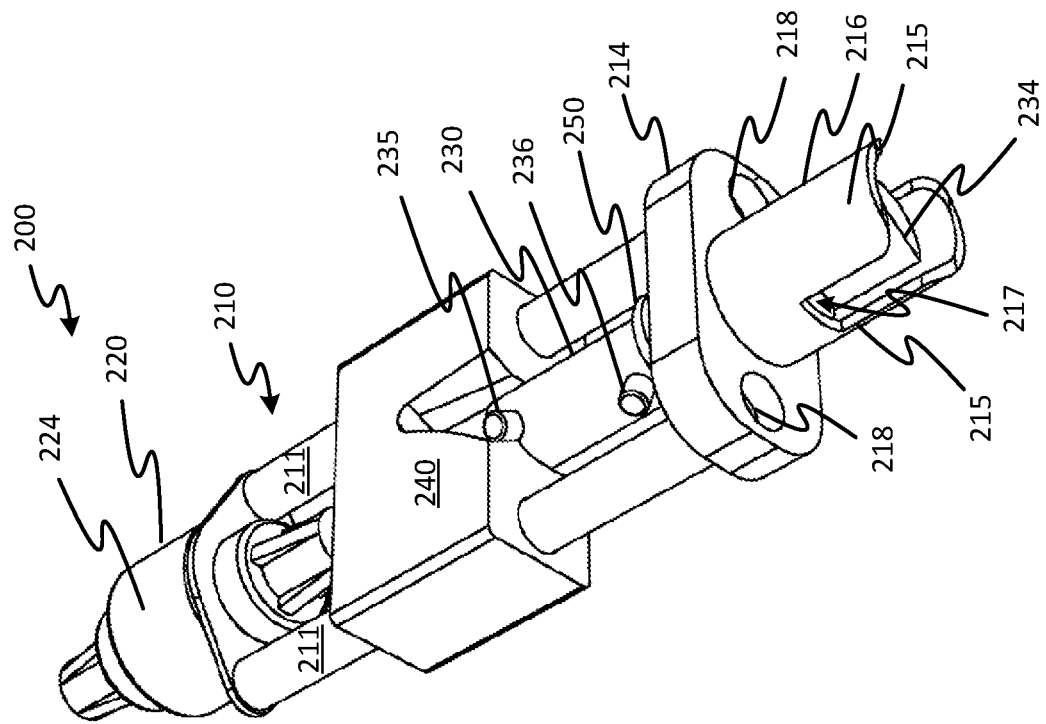
FIGS. 10 and 11 are perspective views of a linearly actuated pinch clamp in open and closed positions, respectively, in accordance with another embodiment of the present disclosure.
Figure 10:
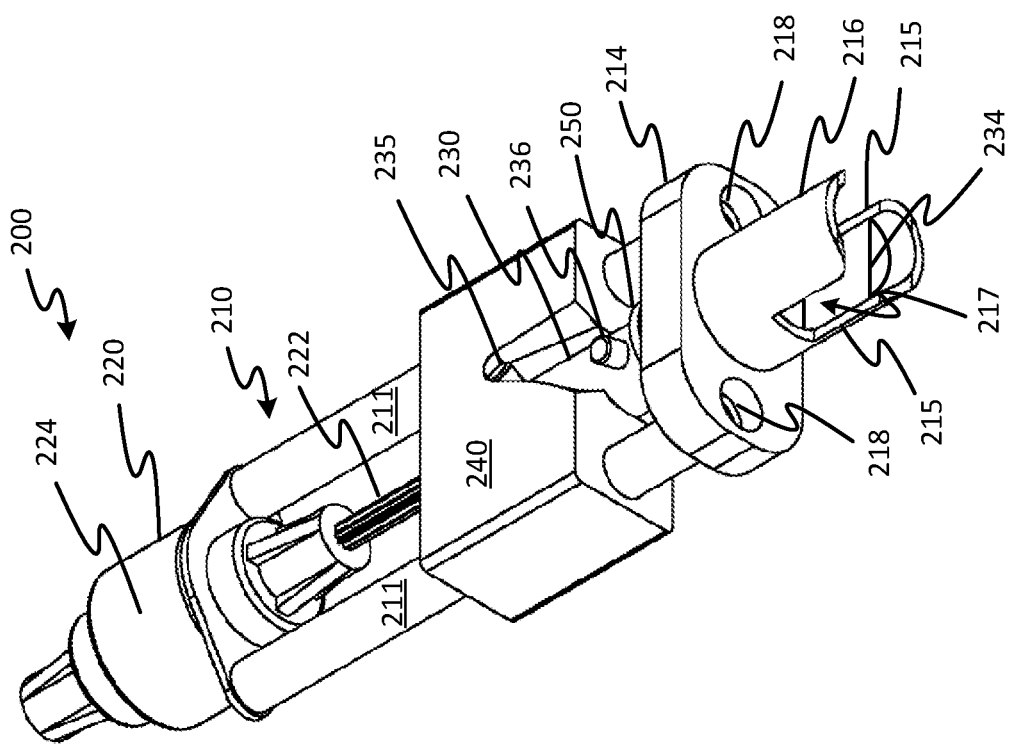
Figure 18:
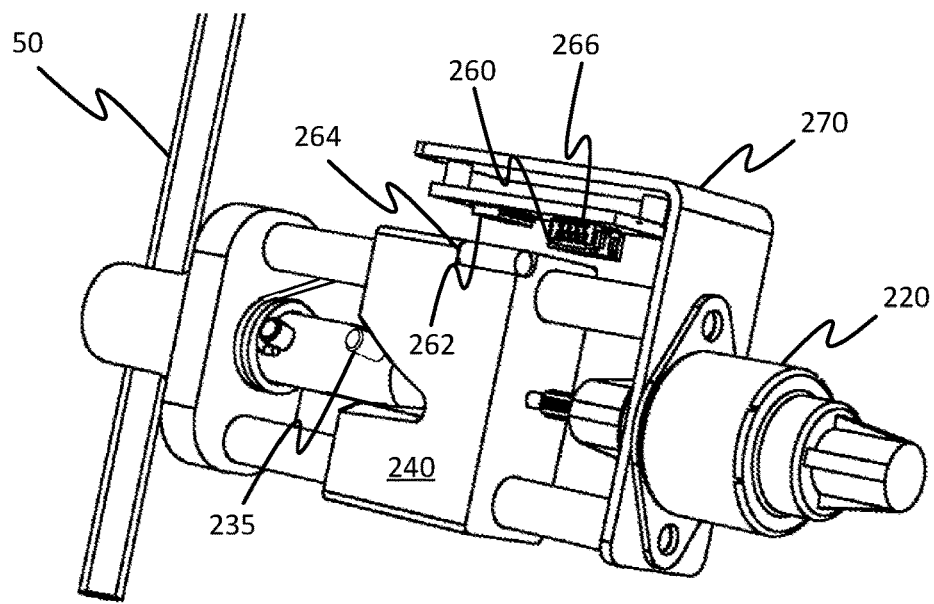
FIG. 18 shows a mounting bracket for a circuit board and sensor that detects the position of the coupling block according to embodiments of the disclosed subject matter

When the pinching element 130 is commanded to the open position shown in FIG. 3, the upper surface 139 of the transverse bore 138 interferingly engages the coupling block pin 146, moving the pinching element 130 thereby causing the spring 150 to be compressed to a first predetermined length $L_1$. When the pinching element 130 is commanded to the closed position, shown in FIG. 4, the spring relaxes to a second predetermined length $L_2$ that is greater than the first predetermined length $L_1$ coming to rest due to interfering engagement of the pinching surface 134 and the squeezed tube 50. The difference between $L_1$ and $L_2$ may be at least the difference between the fully open diameter of the tube 50 and the fully pinched diameter of the tube 50, to permit the tube to be fully open and fully pinched. The difference between $L_1$ and $L_2$ may be between 2 to 20 mm, for example. Advantageously, the arrangement of the spring 150 requires a maximum motor power to be used to open the pinch clamp 100, and a minimum motor force to close the pinch clamp 100.

Additionally, when the pinching element 130 is commanded to the open position, each end of the coupling block pin 146 contacts the upper surface 139 of the transverse bore 138 of the pinching element body 132, and, when the pinching element 130 is commanded to the closed position, preferably neither end of the coupling block pin 146 contacts the upper surface 139 or lower surface 137 of the transverse bore 138. In the closed position, the coupling block 140 is floating, or in a state of equilibrium, within the transverse bore 138 of the pinching element 130 at a point determined by the position and dimensions of the tube 50 and the position of the fixed surface 75. In the closed position, the spring 150 provides all of the force applied to compress the tube 50 and shut off the flow of fluid. In one embodiment, the pinch force provided by the spring 150 in the closed position is about 8 pounds.

The motor/drive unit 120 advantageously maintains the position of the pinching element 130 when the pinch clamp is de-energized and, in one embodiment using a stepper motor linear actuator as motor/drive unit 120, consumes about 3.5 W when changing state, i.e., from open to closed or from closed to open, and 0 W when not changing state, i.e., the static condition. The position may be maintained without power because of the high mechanical advantage ratio between the rotor and pinching element which allows friction in the drive, principally the lead screw (shallow pitch) of the linear motor, to prevent movement.

FIGS. 10-18 depict various views of a linearly actuated pinch clamp 200, in accordance with another embodiment of the present disclosure. The pinch clamp 200 regulates the flow of liquid through a compressible tube (not shown for clarity), and is selectively adjustable to provide an open position and a closed position. In alternative embodiments, the pinch clamp can be adapted for a plurality of intermediate positions for regulating intermediate degrees of patency of a pinched or partially pinched tube.

The pinch clamp 200 includes a housing 210 that has a pair of support shafts 211 attached to a lower plate 214. A circular flange 216 extends from the lower plate 214, with a central bore 217 that extends through the lower plate 214. The flange 216 defines opposing slots 215 through which a compressible tube may be passed according to a method of use of the pinch clamp 200. The lower plate 214 may be attached to the housing support shafts 211 via screws 218, rivets, welding, adhesive, or other attachment means.

A motor/drive unit 220 is attached to housing support shafts 211 via any suitable attachment means, for example a fastener such as a screw. The motor/drive unit 220 has an output shaft 222 and power leads 224. In certain embodiments, the motor/drive unit 220 comprises a stepper motor linear actuator including a bipolar motor, and the power leads 224 include four wires, two for each phase. In other embodiments, a stepper motor linear actuator includes a unipolar motor, and the power leads 224 include six wires, three for each phase.

As described above, in one embodiment, the motor/drive unit 220 is a Haydon Kerk Series 19541-05-905 captive, bipolar stepper motor linear actuator with a 0.544 inch stroke, a 15° step angle and an operating voltage of 5 VDC. Other stepper motor linear actuators may also be used, such as, for example, non-captive, external, unipolar, 12 VDC operating voltage, etc.

A coupling block 240 is slidingly arranged along the housing support shafts 211 via support shaft bores 241, and includes a coupling block 240 defining at least one cam surface 244, best seen in FIG. 12. In a preferred embodiment, two cam surfaces 244 are provided, as depicted in FIGS. 10, 11, 12 and 14. The proximal end of the coupling block 240 is connected to the output shaft 222 of the stepper motor linear actuator 220, using, for example, a threaded connection 245.

A rotationally displaceable pinching element 230 is at least partially enclosed within the coupling block 240 and the housing lower plate flange 216. The pinching element 230 includes a body 232, a pinching projection 234 at a distal end of the body 232, a cam pin 235 disposed through a transverse bore 238 at a proximal end of a body 232 of the pinching element 230, and a spring pin 236 disposed through another transverse bore 238 at about the middle of the body 232. The cam pin 235 cooperates with the coupling block cam surfaces 244 to convert linear motion of the coupling block 240 to rotational motion of the pinching element 230, and the pinching projection 234 cooperates with an edge of one of the lower plate flange slots 215 to pinch the compressible tube closed.

A spring 250, such as, for example, a helical torsion spring, at least partially surrounds the pinching element body 232, and has a proximal end 251 that abuts a portion of one of the housing support shafts 211, and a distal end 252 that abuts the pinching element pin 236. The spring 250 generates a moment that forces the cam pin 235 against the cam surfaces 244 so that they ride therealong causing the body 230 to rotate thereby rotating the pinching projection 234 to pinch a tube aligned within the opposing slots 215. Specifically, tube is pinched between a pinching edge of the pinching projection 234 and a pinching edge of one of the opposing slots 215 under the urging of the spring 250 when the linear position of the linear actuator 220 is retracted such that the cam pin 235 rides the cam surface 244 until the tube is pinched whereupon the cam pin 235 is released from the surface as the tube supports the full force of the spring by resisting the pinching edges of the between the pinching edge of the pinching projection 234 and the pinching edge of the one of the opposing slots 215.

The pinch clamp 200 also includes a bracket 270, connected to the housing 210 between the motor/drive unit 220 and the proximal ends of the housing support shafts 211, which supports a circuit board 260 on which a magnetoresistive sensor 262 is mounted. As discussed above, in one embodiment, the magnetoresistive sensor 262 is a digital position sensor, such as, for example, a Measurement Specialties KMA36 universal magnetic encoder, that indicates the position of the coupling bock 240 by sensing the shape of the magnetic field of an external magnet 264 mounted within a recess 243 in the coupling block 240. In one embodiment, the external magnet 264 is a cylinder magnet, while in another embodiment, the external magnet 264 is a magnetic pole strip. A nominal pole pitch of 5 mm or less may be used; other pole pitches are also contemplated. Power and data connections to and from the magnetoresistive sensor 262 are provided by an electrical connector 266 mounted on circuit board 260.

A microcontroller (not shown for clarity in FIGS. 10-11) is coupled to the pinch clamp 200, via the connector 266, and receives coupling element position measurement data from the magnetoresistive sensor 262. The microcontroller determines the position of the coupling block 240, converts the linear position of the coupling block 240 into a rotational position of the pinching element 230, determines and provides position commands to a motor driver (not shown for clarity in FIGS. 10-11) coupled to the stepper motor linear actuator 220 via power leads 224. The functionality provided by the microcontroller may be incorporated into a microprocessor onboard the device in which the pinch clamp 200 is employed. The motor driver converts the position commands from the microcontroller into drive signals for the stepper motor linear actuator 220, and then provides those drive signals via power leads 224. The motor driver typically includes a power supply, logic and switching circuitry, a clock pulse source, etc., and may be a bipolar drive, a unipolar drive, a constant voltage or an L/R drive, a chopper drive, a microstepping drive, etc. The motor driver is coupled directly or indirectly to a DC supply voltage source. The operation of the microcontroller and motor driver are also explained in more detail below with respect to FIG. 30.

When the pinching element 230 is commanded to the open position, the spring 250 is compressed to a first predetermined angular deflection $\alpha_1$, and, when the pinching element 230 is commanded to the closed position, the spring is compressed to a second predetermined angular deflection $\alpha_2$ that is less than the first predetermined angular deflection $\alpha_1$. The difference between $\alpha_1$ and $\alpha_2$ is related to the maximum diameter of the tube 50 that can be serviced by the pinch clamp 200, which is governed, generally, by the stroke of the motor/drive unit 220, the measurement limits of the magnetoresistive sensor 262, the spring constant of the spring 250, the compressibility of the tube 50, the width of the housing flange slots 217, etc. Advantageously, this arrangement of the spring 250 requires a maximum motor force in order to open the pinch clamp 230, and a minimum motor force in order to close the pinch element 230. In one embodiment, the pinch force provided by the spring 250 in the closed position is about 8 pounds.

The motor/drive unit 220 advantageously maintains the position of the pinching element 230 when the pinch clamp 200 is de-energized, and, in one embodiment where a stepper motor linear actuator is used, consumes about 3.5 W when changing state, i.e., from open to closed or from closed to open, and 0 W when not changing state, i.e., the static condition.

Figure 19:
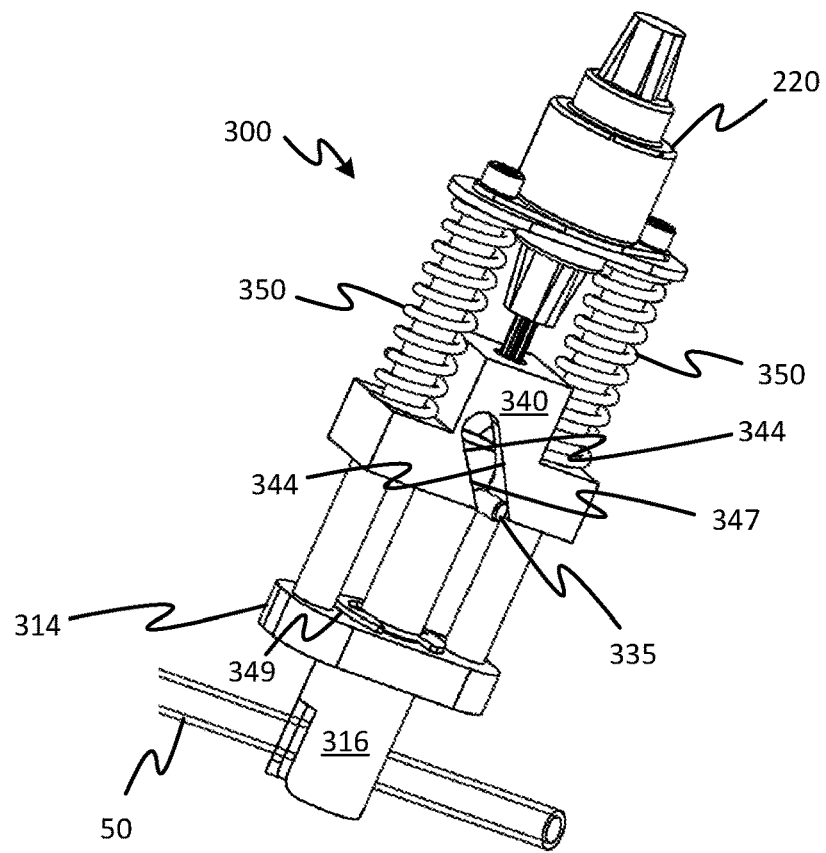
FIG. 19 shows an embodiment in which close and open cam surfaces are provided on a coupling block with the spring force provided by longitudinally-extending coil springs.

FIG. 19 depicts a linearly actuated pinch clamp 300, in accordance with an embodiment of the present disclosure.

The pinch clamp 300 regulates the flow of liquid through a compressible tube 50, and is selectively adjustable to provide an open position and a closed position, and, in certain embodiments, a plurality of intermediate positions.

The pinch clamp 300 includes a housing 310 that has a pair of support shafts 311 and a lower plate 314 including a circular flange 316, with a central bore 317, extending from the lower plate 314. The flange 316 includes opposing slots 315 through which the compressible tube passes. The lower plate 314 is attached to the housing support shafts 311 via screws 318 or other known attachment means. A motor/drive unit 320 is attached to housing support shafts 311 via screws 318 or other known attachment means, and has an output shaft 322 and power leads 324. In certain embodiments, motor/drive unit 320 comprises a stepper motor linear actuator including a bipolar motor, and the power leads 324 include four wires, two for each phase. In other embodiments, the stepper motor linear actuator includes a unipolar motor, and the power leads 324 include six wires, three for each phase.

As described above, in one embodiment, the motor/drive unit 320 is a Haydon Kerk Series 19541-05-905 captive, bipolar stepper motor linear actuator with a 0.544 inch stroke, a 15° step angle and an operating voltage of 5 VDC. Other stepper motor linear actuators may also be used, such as, for example, non-captive, external, unipolar, 12 VDC operating voltage, etc.

A coupling block 340 is slidingly arranged along the housing support shafts 311 via support shaft bores 341, and includes a body 342 defining at least one cam surface 343. In a preferred embodiment, two cam surfaces 343 are provided which engage with cam pin 335. The proximal end of the coupling block 340 is connected to the output shaft 322 of the stepper motor linear actuator 320, using, for example, a threaded connection 345.

Two springs 350, such as, for example, helical compression springs, surround the housing support shafts 311, and have proximal ends 351 that abut portions of the motor/drive unit 320, and distal ends 152 that abut the shoulders 346 of the coupling block 340. In other embodiments, a single helical compression spring 350, surrounding a single support shaft 311 or, alternatively, a single helical compression spring surrounding the output shaft 322 and abutting the upper portion 348 of the coupling block 340, may also be used.

A rotationally displaceable pinching element 330 is at least partially enclosed within the coupling element body 342 and the housing lower plate flange 316. The pinching element 330 includes a body 332, a pinching projection 334 that is similar and functions identically to pinching projection 234 at a distal end of the body 332, and a cam pin 335 disposed through a transverse bore 338 at a proximal end of the body 332. The cam pin 335 cooperates with the coupling block cam surfaces 344 to convert linear motion of the coupling block 340 to rotational motion of the pinching element 330, and the pinching projection 334 cooperates with an edge of one of the lower plate flange slots 315 to pinch the compressible tube 50 closed. A retaining ring groove 331 may be provided in the body 332 to receive a retaining ring.

The pinch clamp 300 also includes a bracket 370, connected to the housing 310 between the motor/drive unit 320 and the proximal ends of the housing support shafts 311, which supports a circuit board 360 on which a magnetoresistive sensor 362 is mounted. As discussed above, in one embodiment, the magnetoresistive sensor 362 is a digital position sensor, such as, for example, a Measurement Specialties KMA36 universal magnetic encoder, that determines the position of the coupling bock 340 by sensing the position of an external magnet 364 mounted within a recess 343 in the coupling block body 342. In one embodiment, the external magnet 364 is a cylinder magnet, while in another embodiment, the external magnet 364 is a magnetic pole strip. A nominal pole pitch of 5 mm or less may be used; other pole pitches are also contemplated. Power and data connections to and from the magnetoresistive sensor 362 are provided by an electrical connector 366 mounted on circuit board 360.

A microcontroller (not shown for clarity in FIGS. 20-21) is coupled to the pinch clamp 300, via the connector 366, and receives coupling element position measurement data from the magnetoresistive sensor 362. The microcontroller determines the position of the coupling block 340, converts the linear position of the coupling block 340 into a rotational position of the pinching element 330, determines and provides position commands to a motor driver (not shown for clarity in FIGS. 20-21) coupled to the motor drive unit 320 via power leads 324. The functionality provided by the microcontroller may be incorporated into a microprocessor onboard the device in which the pinch clamp 300 is employed. The motor driver converts the position commands from the microcontroller into drive signals for the motor/drive unit 320, and then provides those drive signals via power leads 324. The motor driver typically includes a power supply, logic and switching circuitry, a clock pulse source, etc., and may be a bipolar drive, a unipolar drive, a constant voltage or an L/R drive, a chopper drive, a microstepping drive, etc. The motor driver is coupled directly or indirectly to a DC supply voltage source.

When the pinching element 330 is commanded to the open position, the springs 350 are compressed until the block body 342 is detected at a predetermined position. At that position, the pinching element 330 is in the open position of the tube, the springs are compressed to a second predetermined length $L_2$ that is greater than the first predetermined length $L_1$. The difference between $L_1$ and $L_2$ is related to the maximum diameter of the tube 50 that can be serviced by the pinch clamp 300, which is governed, generally, by the stroke of the motor/drive unit 320, the measurement limits of the magnetoresistive sensor 362, the spring constant of the spring 350, the compressibility of the tube 50, the width of the housing flange slots 317, etc. Generally, the difference between $L_1$ and $L_2$ ranges from about 0.1 inches to 1.0 inches; in one embodiment, the difference is about 0.5 inches. Advantageously, this arrangement of the spring 350 requires a maximum motor force in order to open the pinch clamp 300, and a minimum motor force in order to close the pinch clamp 300. In one embodiment, the pinch force provided by the springs 350 in the closed position is about 8 pounds.

The motor/drive unit 320 advantageously maintains the position of the pinching element 330 when the pinch clamp is de-energized, and, in one embodiment where a stepper motor linear actuator is used as the motor/drive unit, consumes about 3.5 W when changing state, i.e., from open to closed or from closed to open, and 0 W when not changing state, i.e., the static condition.

FIG. 30 presents a block diagram of a linearly actuated pinch clamp system 400, in accordance with an embodiment of the present disclosure. Pinch clamp system 400 includes a linearly actuated pinch clamp 100, 200, 300, a motor driver 410 coupled to the pinch clamp 100, 200, 300, a microcontroller 420 coupled to the pinch clamp 100, 200, 300 and the power supply 480, a switch 430 coupled to the microcontroller 420 and the motor driver 410, an energy storage device 440 coupled to the motor driver 410, a voltage boost converter 450 coupled to the energy storage device 440 and the power supply 480, a power fail voltage detector 460 coupled to the switch 430 and the power supply 480, and an oscillator 470 coupled to the switch 430 and the power supply 480. In one embodiment, the microcontroller 420 is directly coupled to the motor driver 410.

Because the pinch clamp 100, 200, 300 nominally retains its currently-commanded position when system power fails, due to the use of the motor/drive units 120, 220, 320, pinch clamp system 400 advantageously provides energy storage and command authority to close the pinch clamp 100, 200, 300 during a system power failure. In one embodiment, voltage boost converter 450 boosts the 24 VDC system voltage provided by power supply 480 to 42 VDC, and provides this boosted voltage level to energy storage device 440 in order to maximize the electrical energy storage. In this embodiment, energy storage device 450 includes one or more conventional capacitors and supporting electronic circuits; those of skill in the art will appreciate that other embodiments may include batteries and associated charging circuits, potential or kinetic energy storage devices and conversion circuits, etc.

The energy storage device 440 provides power to the motor driver 410, which drives the pinch clamp 100, 200, 300 under the direction of commands received from the switch 430. Under normal operation; i.e., when the voltage provided by power supply 480 remains above a predetermined level, the switch 430 passes the position commands received from the microcontroller 420 to the motor driver 410. When power fail voltage detector 460 determines that the power supply voltage has fallen below the predetermined level, a control signal is sent to switch 430. In response to the receipt of the control signal from power fail voltage detector 460, switch 430 discontinues passing commands from the microcontroller 420, and sends a command to close the pinch clamp 100, 200, 300, to motor driver 410. This command is based on a signal received from the oscillator 470. In one embodiment, the power supply voltage is about 24 VDC, and the predetermined threshold voltage is about 20 VDC.

Because the oscillator 470 is coupled to the power supply 480, a reduction in power supply voltage during a power failure may affect the functioning of the oscillator 470. In one embodiment, the oscillator 470 is also coupled to the energy storage device 440 to ensure that the signal is provided to the switch 430 at least until the pinch clamp 100, 200, 300 closes during the system power failure.

FIG. 24 is a block diagram of a valve according to the present disclosure in which an intermediate connection between the mechanical drive and a biased actuator causes the actuator to close the conveyance, thereby avoiding the need for energy storage. The present embodiment is a variant of that disclosed in FIG. 21 which represents functionally and schematically the other embodiments disclosed above. FIG. 24, like FIG. 21, represents a range of possible physical embodiments in which instead of using a power loss detector and an energy storage, a release 1240 that releases the force applied by the mechanical drive 1001 against the biased actuator 1002 such that the biased actuator 1002 is released to close the conveyance 1010. In embodiments, power is applied from a power source 1245 to the motor 1000 and the release 1240. In an embodiment, the release 1240 is an electromagnet and magnetic conductor that when powered-on, can apply a tractive force to the biased actuator 1002 thereby permitting the mechanical drive 1001 to open the conveyance 1010 as in foregoing embodiments.

A clamp 1031 comprises a motor 1000, which, as in prior embodiments, can be a conventional motor, a stepper motor, etc. The output of motor 1000 is connected to drive a mechanical drive unit 1001 that either converts the motion of the motor 1000 to a different kind of motion (e.g., linear-to-rotary or linear-to-curvilinear) with or without force multiplication. The force multiplication may include the generation of mechanical advantage provided by the mechanism of the mechanical drive 1001. Examples of such force-multiplying mechanisms include gear trains, worm drives, cranks, linkages, chain drives, screw drives, etc. The mechanical drive converted mechanical output of the mechanical drive 1001 is applied to an actuator, for example, a pinching element that pinches a flexible tube (which is an example of a conveyance 1010) to block the flow of fluid therethrough, or a valve portion. In particular embodiments, the mechanical drive unit 1001 includes a screw drive, such as used in many linear actuators. In other embodiments, the mechanical drive unit 1001 comprises a set of gears, such as a rack and pinion arrangement. In still further embodiments, the mechanical drive includes a cam and follower arrangement. These embodiments are merely illustrative and may of a variety of different types within the scope of the disclosed and claimed subject matter.

The output of mechanical drive unit 1001 is applied through a release 1240 to a biased actuator 1002 which applies a biasing force of a spring, elastomer, or other equivalent biasing device, to a member that alters the state of the conveyance 1010 to stop a flow therethrough. The arrangement between the biased actuator 1002 and the mechanical drive 1001 is such that the mechanical drive 1001 is able to apply a force against the biasing device to retract and open the fluid conveyance 1010. Power is supplied from a power source 1245 to the motor 1000, the controller 1003, and the release 1240. The conveyance 1010 can be a flexible bag, a tube, or other device for conveying fluid. Preferably the motor 1000 and mechanical drive 1001 are configured such that the spring or other biasing device of the biased actuator 1002 is not able to force itself into a relaxed state when the motor 1000 is at rest. In this way, the motor 1000 can be operated only when the state of the conveyance 1010 is to be altered. In embodiments, the biased actuator 1002 includes a pinching element that is forced against a flexible tube type of conveyance 1010 wherein the tube is pinched in cooperation with a fixed member as in embodiments described herein. In embodiments of clamp 1031, the pinching element may be two opposing pinching elements the open and close in a gripper or scissor fashion to pinch claim tube. In other embodiments, the pinching element may be a single element that cooperates with a fixed stationary element between which the tube is compressed.

In embodiments the pinching element is linearly displaceable. In other embodiments the pinching element is rotationally displaceable. Various kinematic mechanisms can produce combinations or types of motion and may be employed with the pinching element. In any of these embodiments, the pinching element may be a single element that cooperates with a fixed element or may be one of multiple elements that cooperatively pinch the tube. In any of the embodiments biased actuator 1002 may include an urging element such as a spring, elastomer, or arrangement of magnets, effective to produce a biasing force that biases the actuator (e.g., pinching element or elements) to a closed position; i.e., a position that closes the conveyance 1010.

The motor 1000 applies a force to overcome the bias of the urging element thereby permitting the tube (generally, the conveyance 1010) to open. The biasing element may be selected to provide precisely the force, applied to an actuator of the biased actuator 1002 (e.g., pinching element or elements) to ensure a reliable seal of the conveyance 1010 (e.g., flexible tube). Advantageously, the mechanical drive 1001 may be selected such that no power is required to maintain the biased actuator 1001 in the open or closed position. In other words, the motor is deactivated after an open or closed position is reached. In embodiments, this is assured by a suitable selection of the mechanical drive 1001 such that internal friction of the mechanical drive 1001, the motor 1000, and or the biased actuator 1002, or interfering resistance of any or all of these, prevents movement of the biased actuator unless the motor 1000 is used to drive it, except upon power loss, due to the release 1240, as now described.

Figure 25A:
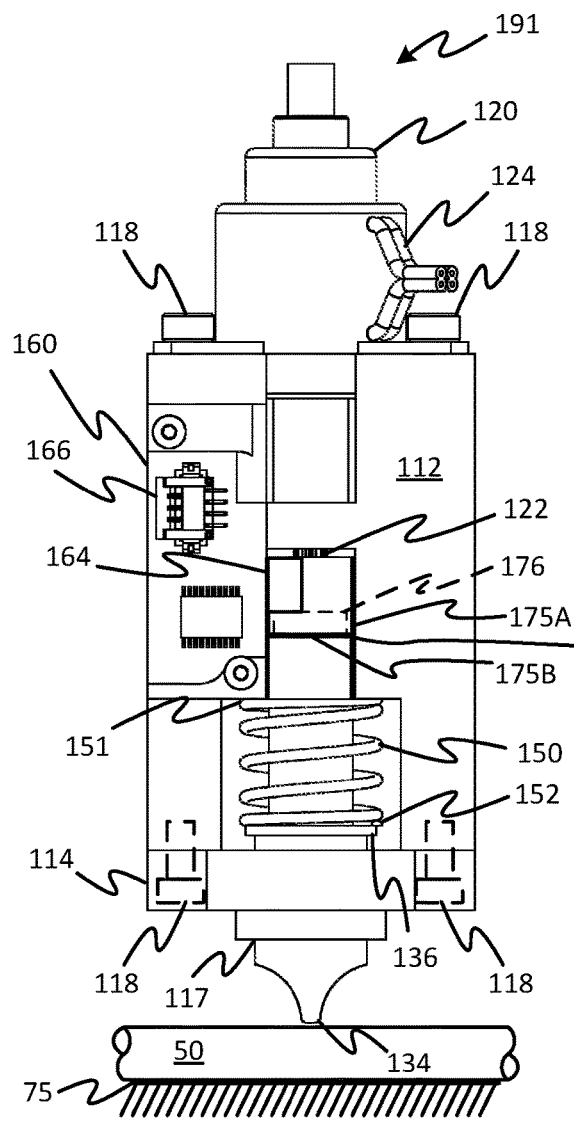
FIGS. 25A and 25B show a pinch clamp embodiment of the valve of FIG. 24 in which an electromagnet is used as a releasable coupling element and otherwise is similar to the embodiment of FIGS. 1-9.

The mechanical drive 1001 forces the biased actuator 1002 against its biasing element to open the conveyance 1010 through a release, which provides at least a part of a mechanical coupling between the mechanical drive and the biased actuator. The release automatically releases (i.e., disengages) this coupling when power is lost from power source 1245. For example, an embodiment of a release includes an electromagnet and magnet circuit element that remain attached when power is supplied to the electromagnet thereby forming a continuous connection between the mechanical drive 1001 and the biased actuator 1002. When power is on, the clamp 1031 operates in the same manner as the embodiment 1030 of FIG. 21 with the motor 1000 transmitting a force to move the biased actuator 1002 to permit flow in the conveyance 1010. That is, the energized electromagnet maintains a connection that allows the force to be transmitted. However, upon power failure, the release 1240 releases (e.g., electromagnet de-energizes) and the biasing element passively moves the actuator of the biased actuator 1002 into the "closed" conveyance position. This obviates the need for an additional power storage device and drive circuit of earlier embodiments. Advantageously, no additional power storage device required for closure in event of power failure. Further, no additional drive circuit is required to close valves in event of power failure. The size and power requirement advantages of earlier embodiments still obtain, that is, high linear travel and thrust force may be accommodated in a smaller, lower cost assembly as compared to solenoid type pinch valves, for example. Also, the present embodiments, allow valves to function as a proportional flow valve (stepper motor allows fine pinching anvil location resolution) that self-closes upon power failure FIG. 25A shows a variant of the embodiments of FIGS. 1-9 but which falls within the description of FIG. 24 and modified accordingly in order to illustrate an example of how the embodiments of FIG. 24 may be implemented. To the extent the description of FIGS. 1-9 does not contradict the following, all the features of the embodiments described with respect to those figures to the embodiment of FIGS. 25A and 25B, including the numbered elements. These features will not be described again hereinbelow, so as to minimize unnecessary repetition. In the pinch clamp 191, pinching element 130 is divided in parts 175A and 175B, with part 175A being coupled to the motor 120 output shaft 122 and part 175B being biased by the spring 150. Power may be transmitted continuously to an electromagnet 176 to maintain a coupling (closed interface between the two parts 175A and 175B shown at 185A) between the pinching element parts 175A and 175B, with the part 175B functioning a magnetic circuit and being of a suitable material for providing such a function. Alternatively, a magnetic circuit element may be embedded in part 175B to perform this function. Power may be conveyed to the electromagnet 176 by means of sliding contacts on part 175A and brushes on housing body 112 or by means of a flexible circuit element or coiled wires. These alternatives and others, being well within the scope of known routine design principles are not elaborated. When power is lost, the electromagnet 176 the coupling force between the parts 175A and 175B is lost and the closed interface 185 opens as indicated at 185B. As a result of the loss of power, the pinching surface of the pinching element part 175B is urged against the flexible tube 50, thereby closing it. To reopen the flexible tube, upon restoration of power, the motor 120 can extend the pinching element part 175A until the electromagnet 176 attaches the pinching element part 175B whereupon the latter may be retracted against the force of the spring 150 causing the flexible tube 50 to open.

Figure 25B:
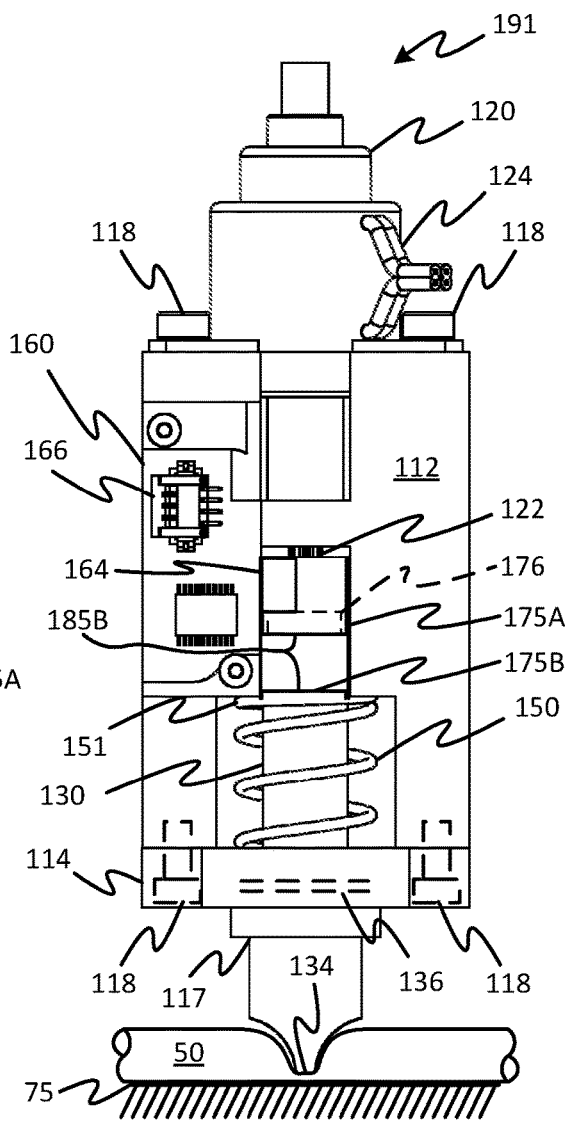

FIGS. 26A and 26B show an alternative arrangement of an electromagnet for a variant of the embodiment of FIGS. 25A and 25B. In FIGS. 25A and 25B, the first 1202 and second 1204 parts of the pinching element are separated proximally of the pinching element magnet 1210 whose position is sensed by a magnetoresistive sensor 1208. In this way, the precise location of the second part 1204 can be determined by a controller for precise positioning. The electromagnet 1206, as in the embodiment of FIGS. 25A and 25B, performs the same function of causing a release of the second part 1204 in the event of a loss of power. In the embodiment of FIG. 26B, an additional magnet 1214 whose position is sensed by a magnetoresistive sensor 1212 is provided. The latter provides feedback to a controller to determine a current position of the pinch element first part 1202, for example to determine a current status to be determined by the controller.

According to first embodiments, a linearly actuated pinch clamp comprises a housing, a motor connected to the housing, a mechanical drive unit connected to the motor for converting a rotary motion of the motor to a linear motion and for introducing a mechanical advantage to the motion of the motor, and a pinching element having a body and a pinching surface. The pinching element body is coupled to the mechanical drive unit and slidably mounted to the housing such that the pinching element is linearly displaceable by the mechanical drive unit between a first position and a second position where the pinching surface cooperates with a fixed surface to pinch closed a flexible tube.

The first embodiments may be revised to form further first embodiments. For example, in such embodiments, the motor includes a rotor, and the mechanical drive unit comprises a nut attached to the rotor and a lead screw threadingly engaged with the nut and coupled to the pinching element.

The first embodiments may be revised to form further first embodiments. For example, in such embodiments, the motor comprises a stepper motor and the mechanical drive unit comprises a screw drive.

The first embodiments may be revised to form further first embodiments. For example, in such embodiments, the pinch clamp comprises a sensor, connected to the housing, to measure a linear position of the pinching element.

The first embodiments may be revised to form further first embodiments. For example, in such embodiments, the sensor is a magneto-resistive sensor, and the pinching element includes a magnet pole strip for cooperating with the sensor to provide an indication of when the pinching element is in the first or second position.

The first embodiments may be revised to form further first embodiments. For example, in such embodiments, a spring is operatively connected between the housing and the pinching element to bias the pinching element toward the second position, thereby reducing a force necessary to move the pinching element from the first position to the second position and pinch closed the flexible tube.

The first embodiments may be revised to form further first embodiments. For example, in such embodiments, the pinching element body comprises a shoulder, and the spring is a helical compression spring at least partially surrounding the pinching element body, the spring having a first end abutting the housing and a second end abutting the pinching element shoulder to bias the pinching element toward the second position.

The first embodiments may be revised to form further first embodiments. For example, in such embodiments, the pinching element body defines a longitudinal bore and a transverse bore, the longitudinal bore partially extending into the body, the transverse bore extending through the body and intersecting the longitudinal bore. The pinching element includes a coupling block, slidingly arranged within the longitudinal bore of the pinching element body, coupled to the stepper motor linear actuator output shaft.

The first embodiments may be revised to form further first embodiments. For example, in such embodiments, the coupling block includes a body, connected to the mechanical drive unit, defining a transverse bore; and a pin, disposed within the transverse bore of the coupling block body, having a length greater than the width of the coupling block body and a diameter smaller than the diameter of the transverse bore of the pinching element body. When the pinching element is disposed in the first position, each end of the pin contacts an upper surface of the transverse bore of the pinching element body and, when the pinching element is disposed in the second position, neither end of the pin contacts the transverse bore of the pinching element body, and the spring maintains the pinching element in the second position.

The first embodiments may be revised to form further first embodiments. For example, in such embodiments, the mechanical drive unit is coupled to the coupling block body via a threaded connector.

The first embodiments may be revised to form further first embodiments. For example, in such embodiments, a motor driver is coupled to the motor; and a microcontroller is coupled to the motor driver and the sensor to command the pinching element to a desired position based on the sensor position measurements.

According to second embodiments, a linearly actuated pinch clamp comprises a housing having a flange, a motor connected to the housing, a mechanical drive unit connected to the motor for converting a rotary motion of the motor to a linear motion and for introducing a mechanical advantage to the motion of the motor; a coupling block including a cam surface, the coupling block connected to the mechanical drive unit and slidably mounted to the housing; and a rotationally displaceable pinching element. The pinching element includes a body rotatably mounted to the housing, a pinching surface at a distal end of the body, and a projection on the body engageable with the coupling block cam surface such that the pinching element is rotationally displaceable by linear motion of the mechanical drive unit and the coupling block between a first position and a second position where the pinching surface cooperates with the housing flange to pinch closed a flexible tube.

The second embodiments may be revised to form further second embodiments. For example, in such embodiments, the motor includes a rotor, and the mechanical drive unit comprises a nut attached to the rotor and a lead screw threadingly engaged with the nut and coupled to the coupling block.

The second embodiments may be revised to form further second embodiments. For example, in such embodiments, the motor comprises a stepper motor and the mechanical drive unit comprises a screw drive.

The second embodiments may be revised to form further second embodiments. For example, in such embodiments, a sensor is attached to the housing to measure a linear position of the coupling block.

The second embodiments may be revised to form further second embodiments. For example, in such embodiments, the sensor is a magneto-resistive sensor, and the coupling block includes a magnet pole strip for cooperating with the sensor to provide an indication of when the pinching element is in the first or second position.

The second embodiments may be revised to form further second embodiments. For example, in such embodiments, a spring is operatively connected between the housing and the pinching element to bias the pinching element toward the second position, thereby reducing a force necessary to move the pinching element from the first position to the second position and pinch closed the flexible tube.

The second embodiments may be revised to form further second embodiments. For example, in such embodiments, the pinching element comprises a pair of the projections, and the coupling block comprises a pair of the cam surfaces that each cooperate with a respective projection of the pinching element.

The second embodiments may be revised to form further second embodiments. For example, in such embodiments, a spring is operatively connected between the housing and the coupling block, and the coupling block cam surface is arranged to engage the pinching element projection such that the spring biases the pinching element toward the second position, thereby reducing a force necessary to move the pinching element from the first position to the second position and pinch closed the flexible tube.

The second embodiments may be revised to form further second embodiments. For example, in such embodiments, the housing includes two support shafts, and the spring comprises two helical compression springs respectively surrounding each support shaft, each helical compression spring having a first end abutting the housing and a second end abutting the coupling block.

The second embodiments may be revised to form further second embodiments. For example, in such embodiments, a motor driver is coupled to the motor; and a microcontroller is coupled to the motor driver and the sensor to command the pinching element to a desired position based on the sensor position measurements.

The second embodiments may be revised to form further second embodiments. For example, in such embodiments, the microcontroller converts the coupling block linear position, measured by the magneto-resistive sensor, to a rotational position of the pinching element.

According to third embodiments, a pinch clamp system includes a power supply, a microcontroller coupled to the power supply; an energy storage device coupled to the power supply; a motor driver coupled to the energy storage device; and a linearly actuated pinch clamp coupled to the motor driver and the microcontroller. The pinch clamp includes a motor, a mechanical drive unit connected to the motor for converting a rotary motion of the motor to a linear motion and for introducing a mechanical advantage to the motion of the motor; a displaceable pinching element coupled to the mechanical drive unit and including a pinching surface, the pinching element being displaceable between a first position and a second position where the pinching surface cooperates with a fixed surface to pinch closed a flexible tube; and a sensor to measure a position of the pinching element. The system further includes a switch, coupled to the power supply, the microcontroller and the motor driver, to pass commands from the microcontroller to the motor driver when the power supply voltage remains above a predetermined threshold, and to provide a command to the motor controller to move the pinching element to the second position when the power supply voltage falls below the predetermined threshold.

The third embodiments may be revised to form further third embodiments. For example, in such embodiments, the pinching element is linearly displaceable.

The third embodiments may be revised to form further third embodiments. For example, in such embodiments, the pinching element is rotationally displaceable and is coupled to the mechanical drive unit via a coupling block that converts the linear motion of the mechanical drive to pinching element rotational displacement.

The third embodiments may be revised to form further third embodiments. For example, in such embodiments, the coupling block includes at least one cam surface, and the pinching element includes a projection that cooperates with the coupling block cam surface.

The third embodiments may be revised to form further third embodiments. For example, in such embodiments, a voltage boost converter is coupled to the power supply and the energy storage device to boost the voltage provided to the energy storage device. A power fail voltage detector is coupled to the power supply and the switch to detect when the power supply voltage falls below the predetermined threshold voltage. An oscillator is coupled to the power supply and the switch to generate a signal to move the pinching element to the second position.

The third embodiments may be revised to form further third embodiments. For example, in such embodiments, the power supply voltage is about 24 VDC, the predetermined threshold voltage is about 20 VDC, and the energy storage device voltage is 42 VDC.

According to fourth embodiments, a pinch clamp includes a motor connected through a mechanical drive unit and a releasable coupling to a pinching element which is biased by a biasing element against a fixed element, a gap between the pinching element and the fixed element receiving a tube that is thereby pinched to with a force determined by the biasing element The coupling element has first and second parts that are connected when power is applied to them and disconnected when power is lost, such that when the motor is driven through the mechanical drive unit to retract the pinching element against the biasing element with power applied to the coupling element, the gap is opened and a tube received therewithin permitted to open and in the event of a loss of power, the releasable coupling releases the second part causing the biasing element to force the pinching element second part to close the tube.

The fourth embodiments may be revised to form further fourth embodiments. For example, in such embodiments, the coupling element includes an electromagnet on one of the pinching element first and second parts and a magnetic circuit on the other of the pinching element first and second parts.

The fourth embodiments may be revised to form further fourth embodiments. For example, in such embodiments, the mechanical drive includes a transmission that increases, through mechanical advantage, a primary force of the motor, whereby a compact size of the motor can be provided.

The fourth embodiments may be revised to form further fourth embodiments. For example, in such embodiments, the mechanical drive includes a linear drive with a lead screw.

According to fifth embodiments, a blood processing system that accepts replaceable disposable fluid circuits comprises one or more pinching devices and a programmable controller. The one or more pinching devices each including a pinch clamp or pinch clamp system according to any of the foregoing embodiments, each pinching device being positioned with respect to a disposable fluid circuit support that removable accepts the fluid circuit and holds it in a predefined orientation and position. The programmable controller being programmed to control the one or more pinching devices to define predefined fluid paths in an attached fluid circuit.

The many features and advantages of the disclosure are apparent from the detailed specification, and, thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

The invention claimed is:

1. A pinch clamp system, comprising:
a power supply;
a microcontroller coupled to the power supply;
an energy storage device coupled to the power supply;
a motor driver coupled to the energy storage device; and
a linearly actuated pinch clamp coupled to the motor driver and the microcontroller, the linearly actuated pinch clamp including at least
a motor,
a displaceable pinching element coupled to the motor driver and including a pinching surface, the displaceable pinching element being displaceable between a first position and a second position where the pinching surface cooperates with a fixed surface to pinch closed a flexible tube;
a mechanical drive unit connected to the motor for converting a rotary motion of the motor to a linear motion and for introducing a mechanical advantage to the rotary motion of the motor, the mechanical drive unit providing coupling between the displaceable pinching element and the motor; and
a sensor to measure a position of the displaceable pinching element;
a switch, coupled to the power supply, the microcontroller and the motor driver, to pass commands from the microcontroller to the motor driver when a voltage of the power supply remains above a predetermined threshold, and to provide a command to the motor driver to move the displaceable pinching element to the second position when the voltage of the power supply falls below the predetermined threshold;
a voltage boost converter, coupled to the power supply and the energy storage device, to boost the voltage provided to the energy storage device; and a power fail voltage detector, coupled to the power supply and the switch, to detect when the voltage of the power supply falls below the predetermined threshold, wherein the displaceable pinching element is rotationally displaceable and is coupled to the mechanical drive unit via a coupling block that converts the linear motion of the mechanical drive unit to pinching element rotational displacement, the coupling block having at least one cam surface, and the displaceable pinching element having a projection that cooperates with the cam surface.

2. The pinch clamp system according to claim 1, wherein the voltage of the power supply is 24 VDC, the predetermined threshold is 20 VDC, and the energy storage device has a voltage of 42 VDC.

3. The pinch clamp system according to claim 1, further comprising:

an oscillator, coupled to the power supply and the switch, to generate a signal to move the displaceable pinching element to the second position.

* * * * *